United States Patent
McSpadden Gardener et al.

(10) Patent No.: US 8,404,475 B2
(45) Date of Patent: Mar. 26, 2013

(54) ISOLATION OF NOVEL BACTERIA CONTRIBUTING TO SOILBORNE DISEASE SUPPRESSION

(75) Inventors: Brian B. McSpadden Gardener, Wooster, OH (US); Maria Soledad Benitez, Quito (EC)

(73) Assignee: The Ohio State University Research Foundation, Columbus, OH (US)

( * ) Notice: Subject to any disclaimer, the term of this patent is extended or adjusted under 35 U.S.C. 154(b) by 130 days.

(21) Appl. No.: 13/055,672

(22) PCT Filed: Jul. 27, 2009

(86) PCT No.: PCT/US2009/051828
§ 371 (c)(1),
(2), (4) Date: Jan. 24, 2011

(87) PCT Pub. No.: WO2010/011990
PCT Pub. Date: Jan. 28, 2010

(65) Prior Publication Data
US 2011/0293570 A1     Dec. 1, 2011

Related U.S. Application Data

(60) Provisional application No. 61/083,766, filed on Jul. 25, 2008.

(51) Int. Cl.
*C12N 1/20* (2006.01)
(52) U.S. Cl. .................................................. 435/252.3
(58) Field of Classification Search ................ 435/252.3
See application file for complete search history.

(56) References Cited

U.S. PATENT DOCUMENTS

2003/0082147 A1   5/2003   Gouge et al.
2005/0008619 A1   1/2005   Park et al.

FOREIGN PATENT DOCUMENTS

KR    2003-0071279 A    9/2003

OTHER PUBLICATIONS

NCBI Reference Sequence, AB021407, Aug. 24, 2000, 6 pages.
NCBI Reference Sequence, AB191209, Jul. 12, 2005, 6 pages.

*Primary Examiner* — Karen Cochrane Carlson
(74) *Attorney, Agent, or Firm* — Standley Law Group LLP

(57) ABSTRACT

Embodiments relate to plant disease suppressive microorganisms and compositions including the same, methods for isolating disease suppressive microorganisms, and methods for controlling plant disease using disclosed compositions and methods.

11 Claims, 5 Drawing Sheets

SEQUENCE LISTING

```
<160> NUMBER OF SEQ ID NOS: 25

<210> SEQ ID NO 1
<211> LENGTH: 17
<212> TYPE: DNA
<213> ORGANISM: Artificial Sequence
<220> FEATURE:
<223> OTHER INFORMATION: Adapter

<400> SEQUENCE: 1
cggtactcag gactcat                                                    17

<210> SEQ ID NO 2
<211> LENGTH: 19
<212> TYPE: DNA
<213> ORGANISM: Artificial Sequence
<220> FEATURE:
<223> OTHER INFORMATION: Adapter

<400> SEQUENCE: 2
gacgatgagt cctgagtac                                                  19

<210> SEQ ID NO 3
<211> LENGTH: 18
<212> TYPE: DNA
<213> ORGANISM: Artificial Sequence
<220> FEATURE:
<223> OTHER INFORMATION: Adapter

<400> SEQUENCE: 3
gatgagtcct gagtaccg                                                   18

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
taacgcgggg caacctggcg a                                               21

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
cagcacggga gcaatcctgg tgg                                             23

<210> SEQ ID NO 6
<211> LENGTH: 19
```

```
<212> TYPE: DNA
<213> ORGANISM: Artificial Sequence
<220> FEATURE:
<223> OTHER INFORMATION: Primer

<400> SEQUENCE: 6
ggagcaatcc tggtggcga                                                   19

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
agagtttgat cctggctcag                                                  20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
acggctacct tgttacgact t                                                21

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
attaccgcgg ctgctgg                                                     17

<210> SEQ ID NO 10
<211> LENGTH: 1299
<212> TYPE: DNA
<213> ORGANISM: Mitsuaria sp.

<400> SEQUENCE: 10
catgcaagtc gaacggtaac gcggggcaac ctggcgacga gtggcgaacg ggtgagtaat       60
atatcggaac gtgcccagtt gtgggggata actgctcgaa agagcagcta ataccgcata      120
cgacctgagg gtgaaagcgg gggatcgcaa gacctcgcgc aattggagcg gccgatatca      180
gattaggtag ttggtggggt aaaggcctac caagccgacg atctgtagct ggtctgagag      240
gacgaccagc cacactggga ctgagacacg gcccagactc ctacgggagg cagcagtggg      300
gaattttgga caatggggc aaccctgatc cagccatgcc gcgtgcggga agaaggcctt      360
cgggttgtaa accgcttttg tcagggaaga aaagactcct actaatactg ggggttcatg      420
acggtacctg aagaataagc accggctaac tacgtgccag cagccgcggt aatacgtagg      480
gtgcaagcgt taatcggaat tactgggcgt aaagcgtgcg caggcggtta tgcaagacag      540
atgtgaaatc cccgggctca acctgggaac tgcatttgtg actgcatggc tagagtacgg      600 tagagggga tggaattccg cgtgtagcag tgaaatgcgt agatatgcgg aggaacaccg      660
atggcgaagg caatcccctg gacctgtact gacgctcatg cacgaaagcg tggggagcaa      720
acaggattag atacccctggt agtccacgcc ctaaacgatg tcaactggtt gttgggaggg      780
tttcttctca gtaacgtagc taacgcgtga agttgaccgc ctggggagta cggccgcaag      840
```

```
gttgaaactc aaaggaattg acggggaccc gcacaagcgg tggatgatgt ggtttaattc    900
gatgcaacgc gaaaaacctt acctaccctt gacatgccag gaatcctgca gagatgtggg    960
agtgctcgaa agagaacctg gacacaggtg ctgcatggcc gtcgtcagct cgtgtcgtga   1020
gatgttgggt taagtcccgc aacgagcgca acccttgtca ttagttgcta cgaaagggca   1080
ctctaatgag actgccggtg acaaaccgga ggaaggtggg gatgacgtca ggtcatcatg   1140
gcccttatgg gtagggctac acacgtcata caatggccgg gacagagggc tgccaacccg   1200
cgagggggag ctaatcccag aaacccggtc gtagtccgga tcgcagtctg caactcgact   1260
gcgtgaagtc ggaatcgcta gtaatcgcgg atcagcttg                           1299
```

<210> SEQ ID NO 11
<211> LENGTH: 1441
<212> TYPE: DNA
<213> ORGANISM: Mitsuaria sp.

<400> SEQUENCE: 11

```
tagagtttga tcctggctca gattgaacgc tggcggcatg ccttacacat gcaagtcgaa     60
cggtaacgcg ggcaacctg gcgacgagtg gcgaacgggt gagtaatata tcggaacgtg    120
cccagttgtg ggggataact gctcgaaaga gcagctaata ccgcatacga cctgagggtg    180
aaagcggggg atcgcaagac ctcgcgcaat tggagcggcc gatatcagat taggtagttg    240
gtggggtaaa ggcctaccaa gccgacgatc tgtagctggt ctgagaggac gaccagccac    300
actgggactg agacacggcc cagactccta cgggaggcag cagtggggaa ttttggacaa    360
tgggggcaac cctgatccag ccatgccgcg tgcgggaaga aggccttcgg gttgtaaacc    420
gcttttgtca gggaagaaaa gactcctact aatactgggg gttcatgacg gtacctgaag    480
aataagcacc ggctaactac gtgccagcag ccgcggtaat acgtagggtg caagcgttaa    540
tcggaattac tgggcgtaaa gcgtgcgcag gcggttatgc aagacagatg tgaaatcccc    600
gggctcaacc tgggaactgc atttgtgact gcatggctag agtacggtag agggggatgg    660
aattccgcgt gtagcagtga aatgcgtaga tatgcggagg aacaccgatg gcgaaggcaa    720 tccccctggac ctgtactgac gatcatgcac gaaaaccggg ggggagcaaa acaggattag    780 atacccctggt agtccacgcc ctaaacgatg tcaactggtt gttgggaggg tttcttctca    840
gtaacgtagc taacgcgtga agttgaccgc ctggggagta cggccgcaag gttgaaactc    900
aaaggaattg acggggaccc gcacaagcgg tggatgatgt ggtttaattc gatgcaacgc    960
gaaaaacctt acctaccctt gacatgccag gaatcctgca gagatgtggg agtgctcgaa   1020
agagaacctg gacacaggtg ctgcatggcc gtcgtcagct cgtgtcgtga gatgttgggt   1080
taagtcccgc aacgagcgca acccttgtca ttagttgcta cgaaagggca ctctaatgag   1140
actgccggtg acaaaccgga ggaaggtggg gatgacgtca ggtcatcatg gcccttatgg   1200
gtagggctac acacgtcata caatggccgg gacagagggc tgccaacccg cgagggggag   1260
ctaatcccag aaacccggtc gtagtccgga tcgcagtctg caactcgact gcgtgaagtc   1320
ggaatcgcta gtaatcgcgg atcagcttgc cgcggtgaag acgttcccgg gtcttgtaca   1380
caccgcccgt caccccctcc agcgggttct gccagaagta gttagcctaa ccgcaagggg   1440
g                                                                  1441
```

<210> SEQ ID NO 12
<211> LENGTH: 1447
<212> TYPE: DNA
<213> ORGANISM: Mitsuaria sp.

<400> SEQUENCE: 12

```
tgatcctggc tcagattgaa cgctggcggc atgccttaca catgcaagtc gaacggtaac    60
gcggggcaac ctggcgacga gtggcgaacg ggtgagtaat atatcggaac gtgcccagtt   120
gtgggggata actgctcgaa agagcagcta ataccgcata cgacctgagg gtgaaagcgg   180
gggatcgcaa gacctcgcgc aattggagcg gccgatatca gattaggtag ttggtggggt   240
aaaggcctac caagccgacg atctgtagct ggtctgagag gacgaccagc cacactggga   300
ctgagacacg gcccagactc ctacgggagg cagcagtggg gaattttgga caatgggggc   360
aaccctgatc cagccatgcc gcgtgcggga agaaggcctt cgggttgtaa accgcttttg   420
tcagggaaga aaagactcct actaatactg ggggttcatg acggtacctg aagaataagc   480
accggctaac tacgtgccag cagccgcggt aatacgtagg gtgcaagcgt taatcggaat   540
tactgggcgt aaagcgtgcg caggcggtta tgcaagacag atgtgaaatc cccgggctca   600
acctgggaac tgcatttgtg actgcatggc tagagtacgg tagaggggga tggaattccg   660
cgtgtagcag tgaaatgcgt agatatgcgg aggaacaccg atggcgaagg caatcccctg   720
gacctgtact gacgctcatg cacgaaagcg tggggagcaa acaggattag ataccctggt   780
agtccacgcc ctaaacgatg tcaactggtt gttgggaggg tttcttctca gtaacgtagc   840
taacgcgtga agttgaccgc ctggggagta cggccgcaag gttgaaactc aaaggaattg   900
acggggaccc gcacaagcgg tggatgatgt ggtttaattc gatgcaacgc gaaaaacctt   960
acctacccctt gacatgccag gaatcctgca gagatgtggg agtgctcgaa agagaacctg  1020
gacacaggtg ctgcatggcc gtcgtcagct cgtgtcgtga gatgttgggt taagtcccgc  1080
aacgagcgca accccttgtca ttagttgcta cgaaagggca ctctaatgag actgccggtg  1140
acaaaccgga ggaaggtggg gatgacgtca ggtcatcatg gcccttatgg gtagggctac  1200
acacgtcata caatggccgg gacagagggc tgccaacccg cgaggggag ctaatcccag   1260
aaacccggtc gtagtccgga tcgcagtctg caactcgact gcgtgaagtc ggaatcgcta   1320
gtaatcgcgg atcagcttgc cgcggtgaat acgttcccgg gtcttgtaca caccgcccgt   1380
cacaccatgg gagcgggttc tgccagaagt agttagccta accgcaaggg gggcgattac   1440
cacggca                                                             1447
```

<210> SEQ ID NO 13
<211> LENGTH: 1364
<212> TYPE: DNA
<213> ORGANISM: Mitsuaria sp.
<220> FEATURE:
<221> NAME/KEY: misc_feature
<222> LOCATION: (1108)..(1108)
<223> OTHER INFORMATION: n is a, c, g or t
<220> FEATURE:
<221> NAME/KEY: misc_feature
<222> LOCATION: (1117)..(1117)
<223> OTHER INFORMATION: n is a, c, g or t
<220> FEATURE:
<221> NAME/KEY: misc_feature
<222> LOCATION: (1133)..(1133)
<223> OTHER INFORMATION: n is a, c, g or t
<220> FEATURE:
<221> NAME/KEY: misc_feature
<222> LOCATION: (1134)..(1134)
<223> OTHER INFORMATION: n is a, c, g or t
<220> FEATURE:
<221> NAME/KEY: misc_feature
<222> LOCATION: (1136)..(1138)
<223> OTHER INFORMATION: n is a, c, g or t
<220> FEATURE:
<221> NAME/KEY: misc_feature

```
<222> LOCATION: (1297)..(1297)
<223> OTHER INFORMATION: n is a, c, g or t
<220> FEATURE:
<221> NAME/KEY: misc_feature
<222> LOCATION: (1299)..(1299)
<223> OTHER INFORMATION: n is a, c, g or t
<220> FEATURE:
<221> NAME/KEY: misc_feature
<222> LOCATION: (1311)..(1311)
<223> OTHER INFORMATION: n is a, c, g or t
<220> FEATURE:
<221> NAME/KEY: misc_feature
<222> LOCATION: (1328)..(1328)
<223> OTHER INFORMATION: n is a, c, g or t

<400> SEQUENCE: 13
agagtttgat cctggctcag attgaacgct ggcggcatgc cttacacatg caagtcgaac     60
ggtaacgcgg gcaacctgg cgacgagtgg cgaacgggtg agtaatatat cggaacgtgc    120
ccagttgtgg gggataactg ctcgaaagag cagctaatac cgcatacgac ctgagggtga    180
aagcggggga tcgcaagacc tcgcgcaatt ggagcggccg atatcagatt aggtagttgg    240
tggggtaaag gcctaccaag ccgacgatct gtagctggtc tgagaggacg accagccaca    300
ctgggactga gacacggccc agactcctac gggaggcagc agtggggaat tttggacaat    360
gggggcaacc ctgatccagc catgccgcgt gcgggaagaa ggccttcggg ttgtaaaccg    420
cttttgtcag ggaagaaaag actcctacta atactggggg ttcatgacgg tacctgaaga    480
ataagcaccg gctaactacg tgccagcagc cgcggtaata cgtagggtgc aagcgttaat    540
cggaattact gggcgtaaag cgtgcgcagg cggttatgca agacagatgt gaaatccccg    600
ggctcaacct gggaactgca tttgtgactg catggctaga gtacggtaga ggggatgga    660 attccgcgtg tagcagtgaa atgcgtagat atgcggagga acaccgatgg cgaaggcaat    720
cccctggacc tgtactgacg ctcatgcacg aaagcgtggg gagcaaacag gattagatac    780
cctggtagtc cacgccctaa acgatgtcaa ctggttgttg ggagggtttc ttctcagtaa    840
cggagctaac gcgtgaagtt gaccgcctgg ggagtacggc cgcaaggttg aaactcaaag    900
gaattgacgg ggacccgcac aagcggtgga tgatgtggtt taattcgatg caacgcgaaa    960
aaccttacct acccttgaca tgccaggaat cctgcagaga tgtgggagtg ctcgaaagag   1020
aacctggaca caggtgctgc atggccgtcg tcagctcgtg tcgtgagatg ttgggttaag   1080
tcccgcaacg agcgcaaccc ttgtcatnag ttgctangaa agggcactct aanncnnncg   1140
gtgacaaacc ggaggaaggt ggggatgacg tcaggtcatc atggccctta tgggtagggc   1200
tacacacgtc atacaatggc cgggacagag ggctgccaac ccgcgagggg gagctaatcc   1260
cagaaacccg gtcgtagtcc ggatcgcagt ctgcaantng actgcgtgaa ntcggaatcg   1320
ctagtaancg cggatcagct tgccgcggtg aatacgttcc cggg                    1364

<210> SEQ ID NO 14
<211> LENGTH: 1396
<212> TYPE: DNA
<213> ORGANISM: Mitsuaria sp.

<400> SEQUENCE: 14
acttctggca gaacccgctc ccatggtgtg acgggcggtg tgtacaagac ccgggaacgt     60
attcaccgcg gcaagctgat ccgcgattac tagcgattcc gacttcacgc agtcgagttg    120
cagactgcga tccggactac gaccgggttt ctgggattag ctcccccctcg cgggttggca   180 gccctctgtc ccggccattg tatgacgtgt gtagccctac ccataagggc catgatgacc    240
tgacgtcatc cccaccttcc tccggtttgt caccggcagt ctcattagag tgcccttcg    300
```

-continued

| | |
|---|---|
| tagcaactaa tgacaagggt tgcgctcgtt gcgggactta acccaacatc tcacgacacg | 360 |
| agctgacgac ggccatgcag cacctgtgtc caggttctct ttcgagcact cccacatctc | 420 |
| tgcaggattc ctggcatgtc aagggtaggt aaggtttttc gcgttgcatc gaattaaacc | 480 |
| acatcatcca ccgcttgtgc gggtccccgt caattccttt gagtttcaac cttgcggccg | 540 |
| tactccccag gcggtcaact tcacgcgtta gctacgttac tgagaagaaa ccctcccaac | 600 |
| aaccagttga catcgtttag ggcgtggact accagggtat ctaatcctgt ttgctcccca | 660 |
| cgctttcgtg catgagcgtc agtacaggtc caggggattg ccttcgccat cggtgttcct | 720 |
| ccgcatatct acgcatttca ctgctacacg cggaattcca tcccctcta ccgtactcta | 780 |
| gccatgcagt cacaaatgca gttcccaggt tgagcccggg gatttcacat ctgtcttgca | 840 |
| taaccgcctg cgcacgcttt acgccagta attccgatta acgcttgcac cctacgtatt | 900 |
| accgcggctg ctggcacgta gttagccggt gcttattctt caggtaccgt catgaacccc | 960 |
| cagtattagt aggagtcttt tcttccctga caaaagcggt ttacaacccg aaggccttct | 1020 |
| tcccgcacgc ggcatggctg gatcagggtt gcccccattg tccaaaattc cccactgctg | 1080 |
| cctcccgtag gagtctgggc cgtgtctcag tcccagtgtg gctggtcgtc ctctcagacc | 1140 |
| agctacagat cgtcggcttg gtaggccttt accccaccaa ctacctaatc tgatatcggc | 1200 |
| cgctccaatt gcgcgaggtc ttgcgatccc ccgctttcac cctcaggtcg tatgcggtat | 1260 |
| tagctgctct ttcgagcagt tatcccccac aactgggcac gttccgatat attactcacc | 1320 |
| cgttcgccac tcgtcgccag gttgccccgc gttaccgttc gacttgcatg tgtaaggcat | 1380 |
| gccgccagcg ttcaat | 1396 |

<210> SEQ ID NO 15
<211> LENGTH: 1386
<212> TYPE: DNA
<213> ORGANISM: Mitsuaria sp.

<400> SEQUENCE: 15

| | |
|---|---|
| tagagtttga tcctggctca gattgaacgc tggcggcatg ccttacacat gcaagtcgaa | 60 |
| cggtaacgcg gggcaacctg gcgacgagtg gcgaacgggt gagtaatata tcggaacgtg | 120 |
| cccagttgtg ggggataact gctcgaaaga gcagctaata ccgcatacga cctgagggtg | 180 |
| aaagcggggg atcgcaagac ctcgcgcaat tggagcggcc gatatcagat taggtagttg | 240 |
| gtggggtaaa ggcctaccaa gccgacgatc tgtagctggt ctgagaggac gaccagccac | 300 |
| actgggactg agacacggcc cagactccta cgggaggcag cagtggggaa ttttggacaa | 360 |
| tgggggcaac cctgatccag ccatgccgcg tgcgggaaga aggccttcgg gttgtaaacc | 420 |
| gcttttgtca gggaagaaaa gactcctact aatactgggg gttcatgacg gtacctgaag | 480 |
| aataagcacc ggctaactac gtgccagcag ccgcggtaat acgtagggtg caagcgttaa | 540 |
| tcggaattac tgggcgtaaa gcgtgcgcag gcggttatgc aagacagatg tgaaatcccc | 600 |
| gggctcaacc tgggaactgc atttgtgact gcatggctag agtacggtag agggggatgg | 660 |
| aattccgcgt gtagcagtga atgcgtagat atgcggagg acaccgatg gcgaaggcaa | 720 |
| tccctggac ctgtactgac gctcatgcac gaaagcgtgg ggagcaaaca ggattagata | 780 |
| ccctggtagt ccacgcccta acgatgtca actggttgtt ggagggttt cttctcagta | 840 |
| acgtagctaa cgcgtgaagt tgaccgcctg gggagtacgg ccgcaaggtt gaaactcaaa | 900 |
| ggaattgacg gggacccgca caagcggtgg atgatgtggt ttaattcgat gcaacgcgaa | 960 |
| aaaccttacc taccccttgac atgccaggaa tcctgcagag atgtgggagt gctcgaaaga | 1020 |

```
gaacctggac acaggtgctg catggccgtc gtcagctcgt gtcgtgagat gttgggttaa    1080
gtcccgcaac gagcgcaacc cttgtcatta gttgctacga aagggcactc taatgagact    1140
gccggtgaca aaccggagga aggtggggat gacgtcaggt catcatggcc cttatgggta    1200
gggctacaca cgtcatacaa tggccgggac agagggctgc aacccgcga ggggagcta     1260 atcccagaaa cccggtcgta gtccggatcg cagtctgcaa ctcgactgcg tgaagtcgga   1320
atcgctagta atcgcggatc agcttgccgc ggtgaatacg ttcccgggtc ttgtacacac   1380
cgcccg                                                               1386
```

<210> SEQ ID NO 16
<211> LENGTH: 1417
<212> TYPE: DNA
<213> ORGANISM: Mitsuaria sp.

<400> SEQUENCE: 16

```
tagagtttga tcctggctca gattgaacgc tggcggcatg ccttacacat gcaagtcgaa     60
cggtaacgcg gggcaacctg gcgacgagtg gcgaacgggt gagtaatata tcggaacgtg   120
cccagttgtg ggggataact gctcgaaaga gcagctaata ccgcatacga cctgagggtg   180
aaagcggggg atcgcaagac ctcgcgcaat tggagcggcc gatatcagat taggtagttg   240
gtggggtaaa ggcctaccaa gccgacgatc tgtagctggt ctgagaggac gaccagccac   300
actgggactg agacacggcc cagactccta cgggaggcag cagtggggaa ttttggacaa   360
tgggggcaac cctgatccag ccatgccgcg tgcgggaaga aggccttcgg gttgtaaacc   420
gcttttgtca gggaagaaaa gactcctact aatactgggg gttcatgacg gtacctgaag   480
aataagcacc ggctaactac gtgccagcag ccgcggtaat acgtagggtg caagcgttaa   540
tcggaattac tgggcgtaaa gcgtgcgca ggcggttatg caagacagat gtgaaatccc    600
cgggctcaac ctgggaactg catttgtgac tgcatggcta gagtacggta gaggggatg   660 gaattccgcg tgtagcagtg aaatgcgtag atatgcggag gaacaccgat ggcgaaggca   720 atccctgga cctgtactga cgctcatgca cgaaagcgtg gggagcaaac aggattagat     780
accctggtag tccacgccct aaacgatgtc aactggttgt tgggagggtt cttctcagt     840 aacgtagcta acgcgtgaag ttgaccgcct ggggagtacg gccgcaaggt tgaaactcaa   900
aggaattgac ggggacccgc acaagcggtg gatgatgtgg tttaattcga tgcaacgcga   960
aaaaccttac ctacccttga catgccagga atcctgcaga gatgtgggag tgctcgaaag  1020
agaacctgga cacaggtgct gcatggccgt cgtcagctcg tgtcgtgaga tgttgggtta   1080
agtcccgcaa cgagcgcaac ccttgtcatt agttgctacg aaagggcact ctaatgagac   1140
tgccggtgac aaaccggagg aaggtgggga tgacgtcagg tcatcatggc ccttatgggt   1200
agggctacac acgtcataca atggccggga cagagggctg ccaacccgcg aggggagct   1260 aatcccagaa acccggtcgt agtccggatc gcagtctgca actcgactgc gtgaagtcgg   1320
aatcgctagt aatcgcggat cagcttgccg cggtgaatac gttcccgggt cttgtacaca   1380
ccgcccgtca ccatgggga gcgggttctg ccagaag                              1417
```

<210> SEQ ID NO 17
<211> LENGTH: 1384
<212> TYPE: DNA
<213> ORGANISM: Mitsuaria sp.

<400> SEQUENCE: 17

```
ggcggtgtgt acaagacccg ggaacgtatt caccgcggca agctgatccg cgattactag    60
```

```
cgattccgac ttcacgcagt cgagttgcag actgcgatcc ggactacgac cgggtttctg      120
ggattagctc ccctcgcgg gttggcagcc ctctgtcccg gccattgtat gacgtgtgta      180
gccctaccca taagggccat gatgacctga cgtcatcccc accttcctcc ggtttgtcac      240
cggcagtctc attagagtgc cctttcgtag caactaatga caagggttgc gctcgttgcg      300
ggacttaacc caacatctca cgacacgagc tgacgacggc catgcagcac ctgtgtccag      360
gttctctttc gagcactccc acatctctgc aggattcctg gcatgtcaag ggtaggtaag      420 gttttttcgcg ttgcatcgaa ttaaaccaca tcatccaccg cttgtgcggg tccccgtcaa      480
ttcctttgag tttcaacctt gcggccgtac tccccaggcg gtcaacttca cgcgttagct      540
acgttactga gaagaaaccc tcccaacaac cagttgacat cgtttagggc gtgggactac      600
cagggtatct aatcctgttt gctccccacg ctttcgtgca tgagcgtcag tacaggtcca      660
ggggattgcc ttcgccatcg gtgttcctcc gcatatctac gcatttcact gctacacgcg      720
gaattccatc cccctctacc gtactctagc catgcagtca caaatgcagt tcccaggttg      780
agcccgggga tttcacatct gtcttgcata accgcctgcg cacgctttac gcccagtaat      840
tccgattaac gcttgcaccc tacgtattac gcgggctgct ggcacgtagt tagccggtgc      900
ttattcttca ggtaccgtca tgaacccca gtattagtag gagtcttttc ttccctgaca      960
aaagcggttt acaacccgaa ggccttcttc ccgcacgcgg catggctgga tcagggttgc     1020
ccccattgtc caaaattccc cactgctgcc tcccgtagga gtctgggccg tgtctcagtc     1080
ccagtgtggc tggtcgtcct ctcagaccag ctacagatcg tcggcttggt aggcctttac     1140
cccaccaact acctaatctg atatcggccg ctccaattgc gcgaggtctt gcgatccccc     1200
gctttcaccc tcaggtcgta tgcggtatta gctgctcttt cgagcagtta tcccccacaa     1260
ctgggcacgt tccgatatat tactcacccg ttcgccactc gtcgccaggt tgccccgcgt     1320
taccgttcga cttgcatgtg taaggcatgc cgccagcgtt caatctgagc caggatcaaa     1380
ctct                                                                  1384
```

<210> SEQ ID NO 18
<211> LENGTH: 1419
<212> TYPE: DNA
<213> ORGANISM: Burkholderia sp.

<400> SEQUENCE: 18

```
gaacgctggc ggcatgcctt acacatgcaa gtcgaacggc agcacggggg caaccctggt       60
ggcgagtggc gaacgggtga gtaatacatc ggaacgtgtc ctgtagtggg ggatagcccg      120
gcgaaagccg gattaatacc gcatacgatc tacggaagaa agcggggat cttcggacct      180 cgcgctgcag gggcggccga tggcagatta gctagttggt ggggtaaagg cctaccaagg      240
cgacgatctg tagctggtct gagaggacga ccagccacac tgggactgag acacggccca      300
gactcctacg ggaggcagca gtggggaatt ttggacaatg ggggcaaccc tgatccagca      360
atgccgcgtg tgtgaagaag gccttcgggt tgtaaagcac ttttgtccgg aaagaaaacc      420
atcgccctaa tatggtggtg gatgacggt accggaagaa taagcaccgg ctaactacgt      480
gccagcagcc gcggtaatac gtagggtgcg agcgttaatc ggaattactg ggcgtaaagc      540
gtgcgcaggc ggtctgttaa gaccgatgtg aaatccccgg gcttaacctg gaactgcat      600 tggtgactgg caggctttga gtgtggcaga gggaggtaga attccacgtg tagcagtgaa      660
atgcgtagag atgtggagga ataccgatgg cgaaggcagc ctcctgggcc aacactgacg      720
ctcatgcacg aaagcgtggg gagcaaacag gattagatac cctggtagtc cacgccctaa      780
```

```
acgatgtcaa ctagttgttg gggattcatt tccttagtaa cgtagctaac gcgtgaagtt      840
gaccgcctgg ggagtacggt cgcaagatta aaactcaaag gaattgacgg ggacccgcac      900
aagcggtgga tgatgtggat taattcgatg caacgcgaaa aaccttacct acccttgaca      960
tggtcggaat cctgctgaga ggcgggagtg ctcgaaagag aaccggcgca caggtgctgc     1020
atggctgtcg tcagctcgtg tcgtgagatg ttgggttaag tcccgcaacg agcgcaaccc     1080
ttgtccttag ttgctacgca agagcactct aaggagactg ccggtgacaa accggaggaa     1140
ggtggggatg acgtcaagtc ctcatggccc ttatgggtag ggcttcacac gtcatacaat     1200
ggtcggaaca gagggttgcc aagccgcgag gcggagccaa tcccagaaaa ccgatcgtag     1260
tccggatcgc agtctgcaac tcgactgcgt gaagctggaa tcgctagtaa tcgcggatca     1320
gcatgccgcg gtgaatacgt tcccgggtct tgtacacacc gcccgtcaca ccatgggagt     1380 gggtttttacc agaagtggct agtctaaccg caaggagga                            1419
```

```
<210> SEQ ID NO 19
<211> LENGTH: 1410
<212> TYPE: DNA
<213> ORGANISM: Burkholderia sp.

<400> SEQUENCE: 19
cggcatgcct tacacatgca agtcgaacgg cagcacgggg gcaaccctgg tggcgagtgg       60
cgaacgggtg agtaatacat cggaacgtgt cctgtagtgg gggatagccc ggcgaaagcc     120
ggattaatac cgcatacgat ctacggaaga aagcggggga tcttcggacc tcgcgctgca     180
ggggcggccg atggcagatt agctagttgg tggggtaaag gcctaccaag gcgacgatct     240
gtagctggtc tgagaggacg accagccaca ctgggactga cacggcccca agactcctac     300
gggaggcagc agtggggaat tttggacaat ggggggcaacc ctgatccagc aatgccgcgt     360
gtgtgaagaa ggccttcggg ttgtaaagca cttttgtccg gaaagaaaac catcgcccta     420
atatggtggt gggatgacgg taccggaaga ataagcaccg gctaactacg tgccagcagc     480
cgcggtaata cgtagggtgc gagcgttaat cggaattact gggcgtaaag cgtgcgcagg     540
cggtctgtta agaccgatgt gaaatccccg gcttaacct  gggaactgca ttggtgactg     600
gcaggctttg agtgtggcag agggaggtag aattccacgt gtagcagtga atgcgtaga      660 gatgtggagg aataccgatg gcgaaggcag cctcctgggc caacactgac gctcatgcac     720
gaaagcgtgg ggagcaaaca ggattagata ccctggtagt ccacgcccta acgatgtca       780 actagttgtt ggggattcat ttccttagta acgtagctaa cgcgtgaagt tgaccgcctg     840
gggagtacgg tcgcaagatt aaaactcaaa ggaattgacg gggacccgca caagcggtgg      900
atgatgtgga ttaattcgat gcaacgcgaa aaaccttacc tacccttgac atggtcggaa     960
tcctgctgag aggcgggagt gctcgaaaga gaaccggcgc acaggtgctg catggctgtc    1020
gtcagctcgt gtcgtgagat gttgggttaa gtcccgcaac gagcgcaacc cttgtcctta    1080
gttgctacgc aagagcactc taaggagact gccggtgaca aaccggagga aggtggggat    1140
gacgtcaagt cctcatggcc cttatgggta gggcttcaca cgtcatacaa tggtcggaac    1200
agagggttgc caagccgcga ggcggagcca tcccagaaaa ccgatcgta gtccggatcg     1260 cagtctgcaa ctcgactgcg tgaagctgga atcgctagta atcgcggatc agcatgccgc    1320
ggtgaataca gttcccgggtc ttgtacacac cgcccgtcac accatgggag tgggttttac    1380
cagaagtggc tagtctaacc gcaaggagga                                      1410
```

```
<210> SEQ ID NO 20
<211> LENGTH: 1419
<212> TYPE: DNA
<213> ORGANISM: Burkholderia sp.
<220> FEATURE:
<221> NAME/KEY: misc_feature
<222> LOCATION: (1364)..(1368)
<223> OTHER INFORMATION: n is a, c, g or t
<220> FEATURE:
<221> NAME/KEY: misc_feature
<222> LOCATION: (1370)..(1370)
<223> OTHER INFORMATION: n is a, c, g or t

<400> SEQUENCE: 20
aacgctggcg gcatgcctta cacatgcmag tcgaacggca gcacgggggc aaccctggtg      60
gcgagtggcg aacgggtgag taatacatcg aacgtgtcc tgtagtgggg gatagcccgg     120
cgaaagccgg attaataccg catacgatct acgaagaaa gcggggatc ttcggacctc      180 gcgctgcagg ggcggccgat ggcagattag ctagttggtg gggtaaaggc ctaccaaggc    240
gacgatctgt agctggtctg agaggacgac cagccacact gggactgaga cacggcccag    300
actcctacgg gaggcagcag tggggaattt tggacaatgg gggcaaccct gatccagcaa    360
tgccgcgtgt gtgaagaagg ccttcgggtt gtaaagcact tttgtccgga agaaaacca    420 tcgccctaat atggtggtgg gatgacggta ccggaagaat aagcaccggc taactacgtg    480
ccagcagccg cggtaatacg tagggtgcga gcgttaatcg gaattactgg gcgtaaagcg    540
tgcgcaggcg gtctgttaag accgatgtga atccccggg cttaacctgg gaactgcatt    600
ggtgactggc aggctttgag tgtggcagag ggaggtagaa ttccacgtgt agcagtgaaa    660
tgcgtagaga tgtggaggaa taccgatggc gaaggcagcc tcctgggcca acactgacgc    720
tcatgcacga aagcgtgggg agcaaacagg attagatacc ctggtagtcc acgccctaaa   780
cgatgtcaac tagttgttgg ggattcattt ccttagtaac gtagctaacg cgtgaagttg    840
accgcctggg gagtacggtc gcaagattaa aactcaaagg aattgacggg acccgcaca     900 agcggtggat gatgtggatt aattcgatgc aacgcgaaaa accttaccta cccttgacat    960
ggtcggaatc ctgctgagag gcgggagtgc tcgaaagaga accggcgcac aggtgctgca    1020
tggctgtcgt cagctcgtgt cgtgagatgt tgggttaagt cccgcaacga gcgcaaccct    1080
tgtccttagt tgctacgcaa gagcactcta aggagactgc cggtgacaaa ccggaggaag    1140
gtggggatga cgtcaagtcc tcatggccct tatgggtagg gcttcacacg tcatacaatg    1200
gtcggaacag agggttgcca agccgcgagg cggagccaat cccagaaaac cgatcgtagt    1260
ccggatcgca gtctgcaact cgactgcgtg aagctggaat cgctagtaat cgcggatcag    1320
catgccgcgg tgaatacgtt cccgggtctt gtacacaccg cccnnnnnan catgggagtg    1380
ggttttacca gaagtggcta gtctaaccgc aaggaggac                           1419

<210> SEQ ID NO 21
<211> LENGTH: 1410
<212> TYPE: DNA
<213> ORGANISM: Burkholderia sp.

<400> SEQUENCE: 21
aacgctggcg gcatgcctta cacatgcaag tcgaacggca gcacgggggc aaccctggtg     60
gcgagtggcg aacgggtgag taatacatcg aacgtgtcc tgtagtgggg gatagcccgg    120
cgaaagccgg attaataccg catacgatct acgaagaaa gcggggatc ttcggacctc     180 gcgctgcagg ggcggccgat ggcagattag ctagttggtg gggtaaaggc ctaccaaggc   240
gacgatctgt agctggtctg agaggacgac cagccacact gggactgaga cacggcccag   300
```

```
actcctacgg gaggcagcag tggggaattt tggacaatgg gggcaaccct gatccagcaa      360
tgccgcgtgt gtgaagaagg ccttcgggtt gtaaagcact tttgtccgga agaaaaccac      420
tcgccctaat atggtggtgg gatgacggta ccggaagaat aagcaccggc taactacgtg      480
ccagcagccg cggtaatacg tagggtgcga gcgttaatcg gaattactgg gcgtaaagcg      540
tgcgcaggcg gtctgttaag accgatgtga atccccggg  cttaacctgg gaactgcatt      600
ggtgactggc aggctttgag tgtggcagag ggaggtagaa ttccacgtgt agcagtgaaa      660
tgcgtagaga tgtggaggaa taccgatggc gaaggcagcc tcctgggcca acactgacgc      720
tcatgcacga aagcgtgggg agcaaacagg attagatacc ctggtagtcc acgccctaaa      780
cgatgtcaac tagttgttgg ggattcattt ccttagtaac gtagctaacg cgtgaagttg      840
accgcctggg gagtacggtc gcaagattaa aactcaaagg aattgacggg acccgcaca       900 agcggtggat gatgtggatt aattcgatgc aacgcgaaaa accttaccta cccttgacat      960
ggtcggaatc ctgctgagag gcgggagtgc tcgaaagaga accggcgcac aggtgctgca     1020
tggctgtcgt cagctcgtgt cgtgagatgt tgggttaagt cccgcaacga gcgcaaccct     1080
tgtccttagt tgctacgcaa gagcactcta aggagactgc cggtgacaaa ccggaggaag     1140
gtggggatga cgtcaagtcc tcatggccct tatgggtagg gcttcacacg tcatacaatg     1200
gtcggaacag agggttgcca agccgcgagg cggagccaat cccagaaaac cgatcgtagt     1260
ccggatcgca gtctgcaact cgactgcgtg aagctggaat cgctagtaat cgcggatcag     1320
catgccgcgg tgaatacgtt cccgggtctt gtacacaccg cccgtcacac catgggagtg     1380
ggttttacca aagtggcta gtctaaccgc                                      1410
```

<210> SEQ ID NO 22
<211> LENGTH: 1417
<212> TYPE: DNA
<213> ORGANISM: Burkholderia sp.
<220> FEATURE:
<221> NAME/KEY: misc_feature
<222> LOCATION: (1368)..(1368)
<223> OTHER INFORMATION: n is a, c, g or t

<400> SEQUENCE: 22

```
acgctggcgg catgccttac acatgcaagt cgaacggcag cacggggggca accctggtgg       60 cgagtggcga acgggtgagt aatacatcgg aacgtgtcct gtagtggggg atagcccggc      120
gaaagccgga ttaataccgc atacgatcta cggaagaaag cggggatct  tcggacctcg      180 cgctgcaggg gcggccgatg gcagattagc tagttggtgg ggtaaaggcc taccaaggcg      240
acgatctgta gctggtctga aggacgacc  agccacactg ggactgagac acggcccaga      300
ctcctacggg aggcagcagt ggggaatttt ggacaatggg ggcaaccctg atccagcaat      360
gccgcgtgtg tgaagaaggc cttcgggttg taaagcactt ttgtccggaa agaaaaccat      420
cgccctaata tggtggtggg atgacggtac cggaagaata agcaccggct aactacgtgc      480
cagcagccgc ggtaatacgt agggtgcgag cgttaatcgg aattactggg cgtaaagcgt      540
gcgcaggcgg tctgttaaga ccgatgtgaa atccccgggc ttaacctggg aactgcattg      600
gtgactggca ggctttgagt gtggcagagg gaggtagaat tccacgtgta gcagtgaaat      660
gcgtagagat gtggaggaat accgatgcg  aaggcagcct cctgggccaa cactgacgct      720
catgcacgaa agcgtgggga gcaaacagga ttagataccc tggtagtcca cgccctaaac      780
gatgtcaact agttgttggg gattcatttc cttagtaacg tagctaacgc gtgaagttga      840
ccgcctgggg agtacggtcg caagattaaa actcaaagga attgacgggg acccgcacaa      900
```

```
gcggtggatg atgtggatta attcgatgca acgcgaaaaa ccttacctac ccttgacatg      960
gtcggaatcc tgctgagagg cgggagtgct cgaaagagaa ccggcgcaca ggtgctgcat     1020
ggctgtcgtc agctcgtgtc gtgagatgtt gggttaagtc ccgcaacgag cgcaacccct     1080
gtccttagtt gctacgcaag agcactctaa ggagactgcc ggtgacaaac cggaggaagg     1140
tggggatgac gtcaagtcct catggccctt atgggtaggg cttcacacgt catacaatgg     1200
tcggaacaga gggttgccaa gccgcgaggc ggagccaatc ccagaaaacc gatcgtagtc     1260
cggatcgcag tctgcaactc gactgcgtga agctggaatc gctagtaatc gcggatcagc     1320
atgccgcggt gaatacgttc ccgggtcttg tacacaccgc ccgtcacncc atgggagtgg     1380
gttttaccag aagtggctag tctaaccgca aggagga                              1417

<210> SEQ ID NO 23
<211> LENGTH: 1384
<212> TYPE: DNA
<213> ORGANISM: Burkholderia sp.
<220> FEATURE:
<221> NAME/KEY: misc_feature
<222> LOCATION: (50)..(50)
<223> OTHER INFORMATION: n is a, c, g or t

<400> SEQUENCE: 23
agtcgaacgg cagcacgggg gcaaccctgg tggcgagtgg cgaacgggtn agtaatacat       60
cggaacgtgt cctgtagtgg gggatagccc ggcgaaagcc ggattaatac cgcatacgat      120
ctacggaaga aagcggggga tcttcggacc tcgcgctgca ggggcggccg atggcagatt      180
agctagttgg tggggtaaag gcctaccaag cgacgatct gtagctggtc tgagaggacg       240
accagccaca ctgggactga gacacggccc agactcctac gggaggcagc agtggggaat      300
tttggacaat gggggcaacc ctgatccagc aatgccgcgt gtgtgaagaa ggccttcggg      360
ttgtaaagca cttttgtccg gaaagaaaac catcgcccta atatggtggt gggatgacgg      420
taccggaaga ataagcaccg gctaactacg tgccagcagc cgcggtaata cgtagggtgc      480
gagcgttaat cggaattact gggcgtaaag cgtgcgcagg cggtctgtta agaccgatgt      540
gaaatccccg ggcttaacct gggaactgca ttggtgactg gcaggctttg agtgtggcag      600
agggaggtag aattccacgt gtagcagtga atgcgtaga gatgtggagg aataccgatg       660
gcgaaggcag cctcctgggc caacactgac gctcatgcac gaaagcgtgg ggagcaaaca      720
ggattagata ccctggtagt ccacgcccta aacgatgtca actagttgtt ggggattcat      780
ttccttagta acgtagctaa cgcgtgaagt tgaccgcctg gggagtacgg tcgcaagatt      840
aaaactcaaa ggaattgacg gggacccgca caagcggtgg atgatgtgga ttaattcgat      900
gcaacgcgaa aaaccttacc taccctagac atggtcggaa tcctgctgag aggcgggagt      960
gctcgaaaga gaaccggcgc acaggtgctg catggctgtc gtcagctcgt gtcgtgagat     1020
gttgggttaa gtcccgcaac gagcgcaacc cttgtcctta gttgctacgc aagagcactc     1080
taaggagact gccggtgaca aaccggagga aggtggggat gacgtcaagt cctcatggcc     1140 cttatggta gggcttcaca cgtcatacaa tggtcggaac agagggttgc caagccgcga     1200
ggcggagcca atcccagaaa accgatcgta gtccggatcg cagtctgcaa ctcgactgcg     1260
tgaagctgga atcgctagta atcgcggatc agcatgccgc ggtgaatacg ttcccgggtc     1320
ttgtacacac cgcccgtcac accatgggag tgggttttac cagaagtggc tagtctaacc     1380
gcaa                                                                  1384
```

<210> SEQ ID NO 24
<211> LENGTH: 1431
<212> TYPE: DNA
<213> ORGANISM: Burkholderia sp.
<220> FEATURE:
<221> NAME/KEY: misc_feature
<222> LOCATION: (1386)..(1386)
<223> OTHER INFORMATION: n is a, c, g or t
<220> FEATURE:
<221> NAME/KEY: misc_feature
<222> LOCATION: (1390)..(1392)
<223> OTHER INFORMATION: n is a, c, g or t

<400> SEQUENCE: 24

| | | | | | |
|---|---|---|---|---|---|
| agtttgatcc | tggctcagat | tgaacgctgg | cggcatgcct | tacacatgca | agtcgaacgg | 60 |
| cagcacgggg | gcaaccctgg | tggcgagtgg | cgaacgggtg | agtaatacat | cggaacgtgt | 120 |
| cctgtagtgg | gggatagccc | ggcgaaagcc | ggattaatac | cgcatacgat | ctacggaaga | 180 |
| aagcggggga | tcttcggacc | tcgcgctgca | ggggcggccg | atggcagatt | agctagttgg | 240 |
| tggggtaaag | gcctaccaag | gcgacgatct | gtagctggtc | tgagaggacg | accagccaca | 300 |
| ctgggactga | gacacggccc | agactcctac | gggaggcagc | agtggggaat | tttggacaat | 360 |
| gggggcaacc | ctgatccagc | aatgccgcgt | gtgtgaagaa | ggccttcggg | ttgtaaagca | 420 |
| cttttgtccg | gaaagaaaac | catcgcccta | atatggtggt | gggatgacgg | taccggaaga | 480 |
| ataagcaccg | gctaactacg | tgccagcagc | cgcggtaata | cgtagggtgc | gagcgttaat | 540 |
| cggaattact | gggcgtaaag | cgtgcgcagg | cggtctgtta | agaccgatgt | gaaatccccg | 600 |
| ggcttaacct | gggaactgca | ttggtgactg | caggctttg | agtgtggcag | agggaggtag | 660 |
| aattccacgt | gtagcagtga | aatgcgtaga | gatgtggagg | aataccgatg | gcgaaggcag | 720 |
| cctcctgggc | caacactgac | gctcatgcac | gaaagcgtgg | ggagcaaaca | ggattagata | 780 |
| ccctggtagt | ccacgcccta | aacgatgtca | actagttgtt | ggggattcat | tccttagta | 840 |
| acgtagctaa | cgcgtgaagt | tgaccgcctg | gggagtacgg | tcgcaagatt | aaaactcaaa | 900 |
| ggaattgacg | gggacccgca | caagcggtgg | atgatgtgga | ttaattcgat | gcaacgcgaa | 960 |
| aaaccttacc | tacccttgac | atggtcggaa | tcctgctgag | aggcgggagt | gctcgaaaga | 1020 |
| gaaccggcgc | acaggtgctg | catggctgtc | gtcagctcgt | gtcgtgagat | gttgggttaa | 1080 |
| gtcccgcaac | gagcgcaacc | cttgtcctta | gttgctacgc | aagagcactc | taaggagact | 1140 |
| gccggtgaca | aaccggagga | aggtggggat | gacgtcaagt | cctcatggcc | cttatgggta | 1200 |
| gggcttcaca | cgtcatacaa | tggtcggaac | agagggttgc | caagccgcga | ggcggagcca | 1260 |
| atcccagaaa | accgatcgta | gtccggatcg | cagtctgcaa | ctcgactgcg | tgaagctgga | 1320 |
| atcgctagta | atcgcggatc | agcatgccgc | ggtgaatacg | ttcccgggtc | ttgtacacac | 1380 |
| cgcccntcan | nncatgggag | tgggttttac | cagaagtggc | tagtctaacc | g | 1431 |

<210> SEQ ID NO 25
<211> LENGTH: 1417
<212> TYPE: DNA
<213> ORGANISM: Burkholderia sp.
<220> FEATURE:
<221> NAME/KEY: misc_feature
<222> LOCATION: (1363)..(1363)
<223> OTHER INFORMATION: n is a, c, g or t
<220> FEATURE:
<221> NAME/KEY: misc_feature
<222> LOCATION: (1368)..(1368)
<223> OTHER INFORMATION: n is a, c, g or t

<400> SEQUENCE: 25

| | | | | | |
|---|---|---|---|---|---|
| acgctggcgg | catgccttac | acatgcaagt | cgaacggcag | cacgggggca | accctggtgg | 60 |

```
cgagtggcga acgggtgagt aatacatcgg aacgtgtcct gtagtggggg atagcccggc      120
gaaagccgga ttaataccgc atacgatcta cggaagaaag cgggggatct tcggacctcg      180
cgctgcaggg gcggccgatg gcagattagc tagttggtgg ggtaaaggcc taccaaggcg      240
acgatctgta gctggtctga gaggacgacc agccacactg ggactgagac acggcccaga      300
ctcctacggg aggcagcagt ggggaatttt ggacaatggg ggcaaccctg atccagcaat      360
gccgcgtgtg tgaagaaggc cttcgggttg taaagcactt ttgtccggaa agaaaaccat      420
cgccctaata tggtggtggg atgacggtac cggaagaata agcaccggct aactacgtgc      480
cagcagccgc ggtaatacgt agggtgcgag cgttaatcgg aattactggg cgtaaagcgt      540
gcgcaggcgg tctgttaaga ccgatgtgaa atccccgggc ttaacctggg aactgcattg      600
gtgactggca ggctttgagt gtggcagagg gaggtagaat tccacgtgta gcagtgaaat      660
gcgtagagat gtggaggaat accgatggcg aaggcagcct cctgggccaa cactgacgct      720
catgcacgaa agcgtgggga gcaaacagga ttagataccc tggtagtcca cgccctaaac      780
gatgtcaact agttgttggg gattcatttc cttagtaacg tagctaacgc gtgaagttga      840
ccgcctgggg agtacggtcg caagattaaa actcaaagga attgacgggg acccgcacaa      900
gcggtggatg atgtggatta attcgatgca acgcgaaaaa ccttacctac ccttgacatg      960
gtcggaatcc tgctgagagg cgggagtgct cgaaagagaa ccggcgcaca ggtgctgcat     1020
ggctgtcgtc agctcgtgtc gtgagatgtt gggttaagtc ccgcaacgag cgcaaccctt     1080
gtccttagtt gctacgcaag agcactctaa ggagactgcc ggtgacaaac cggaggaagg     1140
tggggatgac gtcaagtcct catggccctt atgggtaggg cttcacacgt catacaatgg     1200
tcggaacaga gggttgccaa gccgcgaggc ggagccaatc ccagaaaacc gatcgtagtc     1260
cggatcgcag tctgcaactc gactgcgtga agctggaatc gctagtaatc gcggatcagc     1320
atgccgcggt gaatacgttc ccgggtcttg tacacaccgc ccntcacncc atgggagtgg     1380
gttttaccag aagtggctag tctaaccgca aggagga                              1417
```

ISOLATION OF NOVEL BACTERIA CONTRIBUTING TO SOILBORNE DISEASE SUPPRESSION

CROSS-REFERENCE TO RELATED APPLICATIONS

This application claims priority to U.S. Patent Application No. 61/083,766, filed Jul. 25, 2008, which is hereby incorporated by reference in its entirety.

STATEMENT REGARDING FEDERALLY SPONSORED RESEARCH OR DEVELOPMENT

The present invention was made with United States Government support under grant/contract no. 2002-51106-01935 by the U.S. Department of Agriculture. The United States Government may have certain rights to this invention under 35 U.S.C. §200 et seq.

TECHNICAL FIELD

Embodiments relate to compositions comprising plant disease suppressive microorganisms, methods for isolating disease suppressive microorganisms, and methods for controlling plant diseases using disclosed compositions and microorganisms.

BACKGROUND OF THE ART

Soilborne plant pathogenic fungi and oomycetes cause severe economic losses in the agricultural and horticultural industries. For example, root and crown rot diseases caused by pathogens such as different *Pythium* spp. are a widespread and recurrent problem in plant production. As another example, *Rhizoctonia solani* is a major soilborne fungal phytopathogen, and is associated with diseases such as damping-off, root rot, and leaf and stem rot in many plant species, including greenhouse crops. *R. solani* is also associated with brown patch in creeping bentgrass and various other turfgrasses of high commercial value. Species of *Alternaria* and *Fusarium* are associated with diseases such as early blight of tomato and *Fusarium* wilt of numerous fruit and vegetable crops.

In light of actual and potential environmental and health hazards associated with pesticide use, chemical fungicide use may be restricted. And, certified organic growers may not use synthetic chemicals for pest management. As a result, growers have sought alternative approaches to disease control. These alternative approaches include the use of biological agents and disease-suppressive growing media. The use of biologically active agents in the control of plant pests and diseases has become especially important. Despite the recent commercialization of several types of microbial biocontrol agents, questions still remain about the ability of these agents to provide consistent and reliable control against pathogens.

SUMMARY OF THE INVENTION

Embodiments relate to plant disease suppressive microorganisms, and methods for the isolation of the same. Also disclosed are methods of using the disclosed compositions for controlling plant diseases.

An example embodiment provides a biologically pure strain of a plant disease suppressive microorganism. A preferred embodiment comprises a disease suppressive strain designated H24L5A, deposited as ATCC PTA-10183. An alternative embodiment comprises the disease suppressive strain designated R4F2, deposited as ATCC PTA-10182. In another embodiment, ATCC PTA-10183 and ATCC PTA-10182 are used in combination. Additional embodiments comprise an isolated strain harboring a 16S ribosomal RNA gene comprising at least 97% sequence identity to a sequences identified in Table 2.

Exemplary embodiments also include novel compositions for the biological control of plant pathogens. In some embodiments, a composition may comprise an inert carrier and bacteria of a strain that exhibits fungicidal or fungistatic activity. A composition can also include a growth medium. In other embodiments, the composition may comprise a novel bacterium deposited as ATCC Accession No. PTA-10183. In an alternative embodiment, the composition may comprise a bacterium stain, deposited as ATCC Accession No. PTA-10182. In other embodiments, the composition may comprise ATCC Accession No. PTA-10183 and ATCC Accession No. PTA-10182. In additional embodiments, the composition may comprise an isolated bacterial strain harboring a 16S ribosomal RNA gene comprising at least 97% sequence identity to a sequence identified in Table 2. In various embodiments, compositions may also comprise a growth medium and metabolites produced by the strains noted above.

The novel compositions and methods can be used, for example, to suppress diseases associated with soilborne plant pathogenic fungi, e.g., *Rhizoctonia* species such as *R. solani*. The novel compositions and methods can also be effective in suppressing diseases associated with various plant pathogenic oomycetes (e.g. *Pythium, Phytophthora*), fungi (e.g. *Alternaria, Colletotrichum* and *Fusarium*), and bacteria (e.g. *Pseudomonas, Xanthomonas*).

Exemplary embodiments include methods for the identification and isolation of bacteria responsible for plant disease suppression, particularly novel members of the *Mitsuaria* and *Burkholderia* species. More specifically, various embodiments utilize sequences and terminal restriction fragments (TRF) of 16S rDNA statistically associated with damping-off disease suppression to identify and isolate bacteria giving rise to those TRF.

Accordingly, embodiments provide a method for the isolation of bacteria contributing to soilborne plant disease suppression comprising:

a) identifying a terminal restriction fragment (TRF) of 16S rDNA statistically associated with a soilborne plant disease suppression activity;

b) cloning the TRF identified in step (a) to obtain a cloned TRF;

c) sequencing the TRF identified in step (a) to obtain a TRF sequence;

d) selecting a TRF primer specific to the cloned TRF;

e) selecting a downstream 16S rDNA primer;

f) screening pools of cultured isolates using the TRF specific primer and the a downstream 16S rDNA primer for the presence of an amplification product;

g) sequencing the 16S rDNA of an amplification-product-positive colony to obtain a colony specific sequence;

h) comparing the colony specific sequence to the TRF sequence; and i) isolating the amplification-product-positive colony if the sequences in step (h) are essentially identical.

In another aspect, embodiments feature compositions comprising a bacterial strain that exhibits fungicidal or fungistatic activity combined with an inert carrier. The bacterial strain is present at about $10^5$ cfu to about $10^{11}$ cfu per gram of carrier. Such a composition can be in the form of a granule, wettable powder, or liquid concentrate. In some embodiments, the bacterial strain(s), e.g., the bacterial strains deposited as ATCC Accession No. PTA-10183, ATCC Accession No. PTA-10182, or a combination thereof, exhibits fungicidal or fungistatic activity towards a fungal plant pathogen. The pathogens against which fungicidal or fungistatic activity is observed can be, for example, a species of *Rhizoctonia, Pythium, Phytophthora, Fusarium, Alternataria*, or *Colletotrichum*.

The invention also features a method of controlling or suppressing the growth of a plant pathogenic fungus. In some embodiments, the method comprises applying an effective amount of a bacterial strain designated ATCC Accession No. PTA-10183, ATCC Accession No. PTA-10182, or a combination thereof, to an environment in which the plant pathogenic fungus may grow. Additional embodiments comprise applying an effective amount of a bacterial strain harboring a 16S ribosomal RNA gene comprising at least 97% sequence identity to a sequences identified in Table 2. In other embodiments, the method comprises applying an effective amount of a composition to an environment in which the plant pathogenic fungus may grow. Such a composition comprises a bacterial strain that exhibits fungicidal or fungistatic activity combined with an inert carrier. The composition can include a growth medium and metabolites of the bacterial strains noted above. The fungus may be a species of *Rhizoctonia, Pythium, Phytophthora, Fusarium, Alternataria*, or *Colletotrichum*.

Various embodiments also feature a method of controlling the growth of a plant pathogenic fungus. The method involves applying a composition to a plant. The composition comprises a bacterial strain that exhibits fungicidal or fungistatic activity combined with an inert carrier and, optionally, bacterial metabolites and/or a growth medium. The bacterial strain may be ATCC Accession No. PTA-10183, ATCC Accession No. PTA-10182, or a combination thereof. In additional embodiments, the composition may comprise an isolated bacterial strain harboring a 16S ribosomal RNA gene comprising at least 97% sequence identity to a sequence identified in Table 2. In the method, symptoms of a disease caused by the fungus are ameliorated or suppressed on the plant. The composition can be applied to the leaves or stem of the plant, e.g., the leaves or the stem of a vegetable crop.

Embodiments also features a method of controlling the growth of a plant pathogenic fungus, which comprises applying a composition to seed or soil. The composition comprises a bacterial strain that exhibits fungicidal or fungistatic activity combined with an inert carrier and, optionally, bacterial metabolites and/or a growth medium. The bacterial strain can be ATCC Accession No. PTA-10183, ATCC Accession No. PTA-10182, or a combination thereof. In additional embodiments, the composition may comprise an isolated bacterial strain harboring a 16S ribosomal RNA gene comprising at least 97% sequence identity to a sequence identified in Table 2. In the method, symptoms of a disease associated with the fungus are ameliorated or suppressed on a plant growing in the soil. The fungus can be a species of *Rhizoctonia, Pythium, Phytophthora, Fusarium, Alternataria*, or *Colletotrichum*.

BRIEF DESCRIPTION OF THE BIOLOGICAL DEPOSITS AND SEQUENCE DESCRIPTIONS

The various embodiments of the invention can be more fully understood from the following detailed description, biological deposits, and the accompanying sequence descriptions, which form a part of this application.

Applicants made the following biological deposits under the terms of the Budapest Treaty on the International Recognition of the Deposit of Microorganisms for the Purposes of Patent Procedure:

| Depositor Identification Reference | International Depository Designation | Date of Deposit |
|---|---|---|
| H24L5A | PTA-10183 | Jul. 8, 2009 |
| R4F2 | PTA-10182 | Jul. 8, 2009 |

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Primers and oligonucleotide adapters

| Description | Name | Sequence (SEQ ID NO ) |
|---|---|---|
| MspI TRF cloning | MspI-adapter 1 | 5'-CGGTACTCAGGACTCAT-3' (SEQ ID NO: 1) |
| | MspI-adapter 2 | 5'-GACGATGAGTCCTGAGTAC-3' (SEQ ID NO: 2) |
| | MspI-adapter primer | 5'-GATGAGTCCTGAGTACCG-3' (SEQ ID NO: 3) |
| Variable loop-specific | M139F | 5'-TAACGCGGGGCAACCTGGCGA-3' (SEQ ID NO: 4) |
| | M141F | 5'-CAGCACGGGAGCAATCCTGGTGG-3' (SEQ ID NO: 5) |
| | M141-F2 | 5'-GGAGCAATCCTGGTGGCGA-3' (SEQ ID NO: 6) |
| 16S amplification | 8F | 5'-AGAGTTTGATCCTGGCTCAG-3' (SEQ ID NO: 7) |
| | 1492R | 5'-ACGGCTACCTTGTTACGACTT-3' (SEQ ID NO: 8) |
| | 518R | 5'-ATTACCGCGGCTGCTGG-3' (SEQ ID NO: 9) |

While the primer sequences and adapters identified in Table 1 were used in the examples below, it is appreciated that embodiments include all primers that might reasonably bind to the 16S sequences listed as SEQ ID NOS: 10-25.

SEQ ID NOs: 10-25 are the nucleotide sequences of the 16S rRNA genes of plant disease suppressive strains, isolated as described in the examples below.

TABLE 2

| SEQ ID | Genbank Accession Number | Sequence Description | Corresponding Isolate Designation |
|---|---|---|---|
| SEQ ID NO 10 | EU714905 | *Mitsuaria* sp. 16S ribosomal RNA gene, partial sequence | H24L5A (PTA-10183) |

TABLE 2-continued

| SEQ ID | Genbank Accession Number | Sequence Description | Corresponding Isolate Designation |
|---|---|---|---|
| SEQ ID NO 11 | EU714906 | *Mitsuaria* sp. 16S ribosomal RNA gene, partial sequence | H24L3B |
| SEQ ID NO 12 | EU714907 | *Mitsuaria* sp. 16S ribosomal RNA gene, partial sequence | H23L1 |
| SEQ ID NO 13 | EU714908 | *Mitsuaria* sp. 16S ribosomal RNA gene, partial sequence | H24L2C2 |
| SEQ ID NO 14 | EU714909 | *Mitsuaria* sp. 16S ribosomal RNA gene, partial sequence | H24L1B |
| SEQ ID NO 15 | EU714910 | *Mitsuaria* sp. 16S ribosomal RNA gene, partial sequence | H24L1C |
| SEQ ID NO 16 | EU714911 | *Mitsuaria* sp. 16S ribosomal RNA gene, partial sequence | H24L6B |
| SEQ ID NO 17 | EU714912 | *Mitsuaria* sp. 16S ribosomal RNA gene, partial sequence | H29L1B |
| SEQ ID NO 18 | EU714913 | *Burkholderia* sp. 16S ribosomal RNA gene, partial sequence | R2G3 |
| SEQ ID NO 19 | EU714914 | *Burkholderia* sp. 16S ribosomal RNA gene, partial sequence | R4F2 (PTA-10182) |
| SEQ ID NO 20 | EU714915 | *Burkholderia* sp. 16S ribosomal RNA gene, partial sequence | R4G3 |
| SEQ ID NO 21 | EU714916 | *Burkholderia* sp. 16S ribosomal RNA gene, partial sequence | R4C3 |
| SEQ ID NO 22 | EU714917 | *Burkholderia* sp. 16S ribosomal RNA gene, partial sequence | R4F3 |
| SEQ ID NO 23 | EU714918 | *Burkholderia* sp. 16S ribosomal RNA gene, partial sequence | R4A2 |
| SEQ ID NO 24 | EU714919 | *Burkholderia* sp. 16S ribosomal RNA gene, partial sequence | R4E2 |
| SEQ ID NO 25 | EU714920 | *Burkholderia* sp. 16S ribosomal RNA gene, partial sequence | R2C2 |

Other features and advantages will be apparent from the following detailed description, and from the claims.

BRIEF DESCRIPTION OF THE DRAWINGS

A better understanding of the embodiments will be obtained from a reading of the following detailed description and the accompanying drawings in which.

DETAILED DESCRIPTION OF A PREFERRED EMBODIMENT

Figure 1:
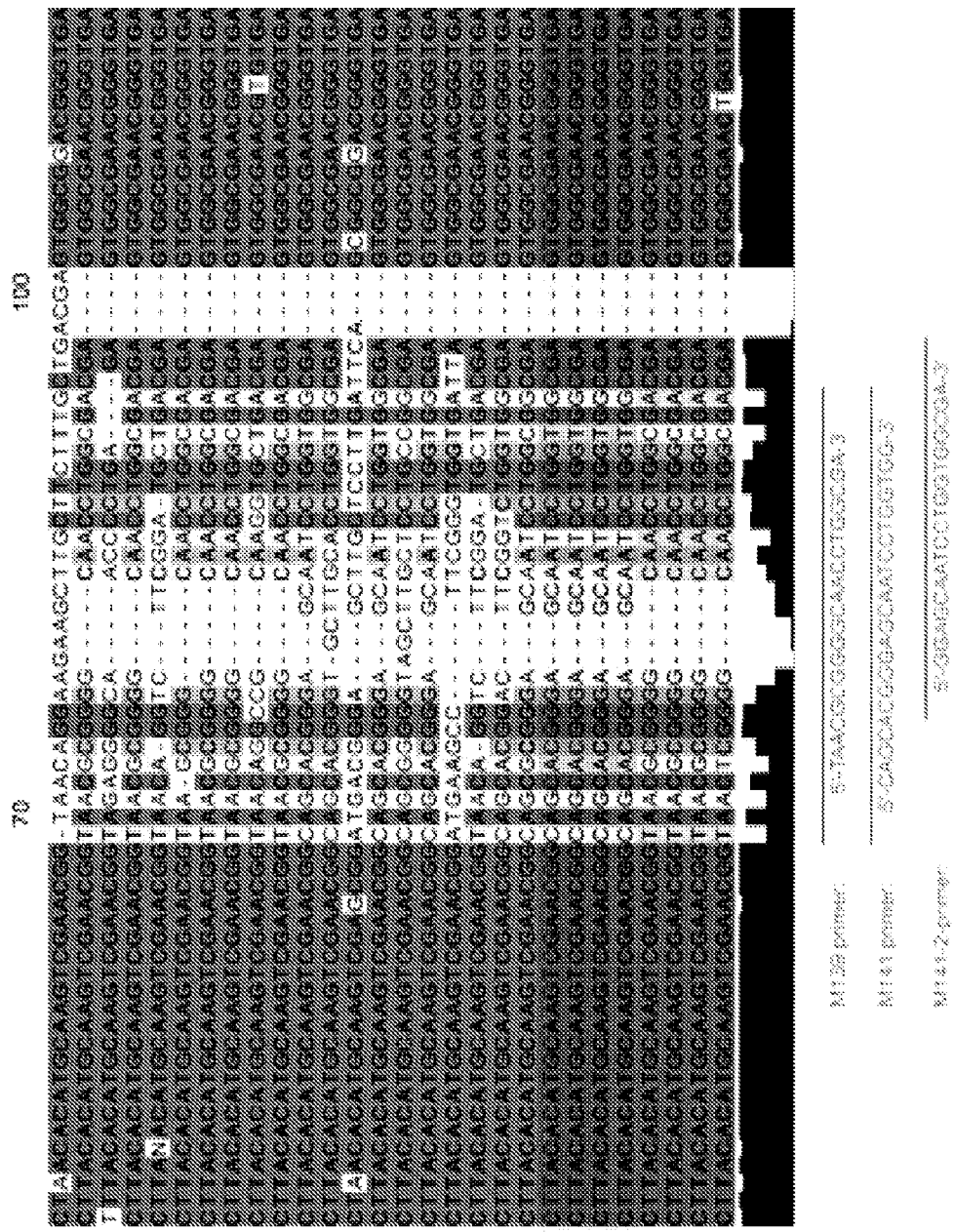
FIG. 1 is a DNA-sequence alignment showing the position and variation of the first variable region of the 16S rRNA of representative species within the order Burkholderiales and clones generated in this study. *E. coli* sequence is shown as a reference, with the variable loop between positions 69 and 101. Primers were designed for this region. Primer sequences and overlap are shown below the alignment.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

A sequence-directed culturing strategy was developed using TRF-derived markers and media reported to be selective for the genera identified. Using exemplary methods, novel *Mitsuaria* and *Burkholderia* species with high levels of sequence similarity to the targeted TRF were isolated and purified. The isolated species inhibit growth of multiple plant pathogens, and usually suppress soybean and tomato seedling diseases. Two embodiments, which are believed to include *Mitsuaria* and *Burkholderia* stains, were deposited as ATCC Accession No. PTA-10183, ATCC Accession No. PTA-10182, respectively. Both strains displayed the targeted function by reducing fungal and oomycete plant pathogen growth in vitro, and reducing disease severity of infected tomato and soybean seedlings.

Embodiments include isolated and purified bacterial strains involved in plant pathogen suppression. Specific embodiments include bacterial strains deposited as ATCC Accession No. PTA-10183 and ATCC Accession No. PTA-10182. Embodiments of the invention also include other strains identified in Table 2. Furthermore, embodiments include other strains harboring a 16S ribosomal RNA gene comprising at least 97% sequence identity to the strains identified in Table 2. For example, at least one embodiment includes a biologically pure culture of a bacterial strain comprising a nucleic acid, the nucleic acid comprising a 16S ribosomal RNA gene sequence at least 97% identical to SEQ ID NO: 10, the bacterial strain exhibits plant pathogen suppression when applied to plant material or a soil environment. Furthermore, at least one embodiment includes a biologically pure culture of a bacterial strain comprising a nucleic acid, the nucleic acid comprising a 16S ribosomal RNA gene sequence at least 97% identical to SEQ ID NO: 19, the bacterial strain exhibits plant pathogen suppression when applied to plant material or a soil environment. Rather, specific embodiments encompasses bacteria containing nucleic acid molecules carrying modifications such as substitutions, small deletions, insertions, or inversions, which nevertheless are at least 97% identical (e.g., at least 98% or 99% identical) to the nucleotide sequence shown as SEQ ID NOs: 10 and 19 in the Sequence Listing.

The determination of percent identity or homology between two sequences is accomplished using the algorithm of Karlin and Altschul (1990) Proc. Nat'l Acad. Sci. USA 87: 2264-2268, modified as in Karlin and Altschul (1993) Proc. Nat'l Acad. Sci. USA 90:5873-5877. Such an algorithm is incorporated into the NBLAST and XBLAST programs of Altschul et al. (1990) J. Mol. Biol. 215:403-410. BLAST nucleotide searches are performed with the NBLAST program, score=100, wordlength=12 to obtain nucleotide sequences homologous to the nucleic acid molecules of the invention. BLAST protein searches are performed with the XBLAST program, score=50, wordlength=3 to obtain amino acid sequences homologous to the protein molecules of the invention. To obtain gapped alignments for comparison purposes, Gapped BLAST is utilized as described in Altschul et al. (1997) Nucleic Acids Res. 25:3389-3402. For the purposes of this disclosure, determinations of percent identity are computed using the default parameters of BLASTIN optimized for highly similar sequences (i.e. megablast) of the respective programs (eg., XBLAST and NBLAST). See The National Center for Biotechnology Information, U.S. National Library of Medicine, Bethesda, Maryland, USA for BLAST programs.

Furthermore, various embodiments include compositions and methods for utilizing the identified strains.

Embodiments also include methods for identifying and isolating bacterial strains involved in plant pathogen suppression. Various methods utilize T-RFLP, in conjunction with various other molecular techniques described below, to direct the recovery of novel disease suppressive microbes.

In various embodiments, ATCC Accession No. PTA-10183 and/or ATCC Accession No. PTA-10182 can be used as a solid. For example, a culture of ATCC Accession No. PTA-10183 and/or ATCC Accession No. PTA-10182 is grown in a suitable growth medium, the bacteria separated from the spent medium, resuspended in a fresh medium and the bacteria spray-dried. The resulting powder can be used, e.g., as a dusting biocontrol agent on vegetable crops. Alternatively, ATCC Accession No. PTA-10183 and/or ATCC Accession No. PTA-10182 can be used as a liquid, e.g., a culture of ATCC Accession No. PTA-10183 and/or ATCC Accession No. PTA-10182 can be grown in a suitable growth medium, the bacteria separated from the spent medium, and resuspended in water, buffer or fresh medium. The resulting suspension can be used, for example, as a foliar spray.

In other embodiments, ATCC Accession No. PTA-10183 and/or ATCC Accession No. PTA-10182 can be combined with one or more compounds to form a mixture suitable for applying to an environment in which a plant pathogenic fungus can grow. Compounds that can be combined with ATCC Accession No. PTA-10183 and/or ATCC Accession No. PTA-10182 bacteria include fertilizers, micronutrient donors, surfactants, or adjuvants conventionally employed in the art of formulation. See, e.g., U.S. Pat. Nos. 6,280,719; 5,780,023; 5,765,087; 5,348,742; and 5,068,105. The number of compounds selected for a given mixture may be chosen in accordance with the intended application and/or existing conditions.

The resulting mixture can be a solid or a liquid, e.g., an emulsifiable concentrate, a coatable paste, a directly sprayable solution, a dilutable solution, a dilute emulsion, a wettable powder, a dusting powder, a granular formulation, or an encapsulated formulation.

ATCC Accession No. PTA-10183 and/or ATCC Accession No. PTA-10182 are effective biological control organisms that have fungicidal activity, and may also have fungistatic activity. The isolated embodiments provide good fungal disease suppression. The use of ATCC Accession No. PTA-10183 and/or ATCC Accession No. PTA-10182 as a biocontrol agent may reduce or eliminate the use of environmentally harmful chemical fungicides, especially those derived from petroleum precursors.

Compositions

In various embodiments, bacteria can be combined with an inert carrier to form a composition suitable for applying to soil. For example, compositions comprising ATCC Accession No. PTA-10183 and/or ATCC Accession No. PTA-10182 can be made in accordance with those described in U.S. Pat. No. 6,995,007, incorporated by reference in its entirety.

Bacteria for use in a composition of the invention exhibit fungicidal or fungistatic activity against one or more fungal pathogens of plants. For example, bacteria exhibiting fungicidal or fungistatic activity against a fungal plant pathogen can be used to inhibit growth of that pathogen and thus provide effective biological control.

It is contemplated that a proportion of the bacteria in exemplary compositions can be relatively innocuous bacterial strains that do not exhibit significant fungicidal or fungistatic activity. Relatively innocuous bacterial strains may be advantageous in some embodiments, e.g., as a marker for persistence in the environment or as a marker for effective coverage following spray application of a composition.

In some embodiments, a growth medium is also included in the composition, e.g., a composition of the invention includes bacteria, porous ceramic particles and a growth medium. Without being bound by theory, it is believed that a composition that includes a growth medium provides the bacterium with a nutrient-rich micro-environment, resulting in a competitive advantage to bacteria present in the composition compared to native soil bacteria thus enabling bacteria of the composition to function more effectively as biocontrol agents.

In some embodiments, an amount of water is present in the composition. For liquid concentrates, water is up to 99% by weight.

Methods of Suppressing Fungal Disease

The invention also features a method comprising applying a composition of the invention to an environment in which a plant pathogenic fungus may grow. Such an environment can be soil, a plant seed, a plant, or a plant part (e.g., leaves, roots, branches and stems). The composition typically is applied in an amount effective to control or suppress fungal growth, e.g., in an amount sufficient to control or suppress observable symptoms on a plant of a fungal disease. The rate of application may vary according to the plant species to be protected, the efficacy of the bacterial strain against the pathogen to be controlled, and the severity of the disease pressure. Typically, the rate of application is about $1.3 \times 10^3$ cfu/cm$^2$ to about $1.3 \times 10^8$ cfu/cm$^2$ of soil or plant surface area, or about or about $1.3 \times 10^3$ cfu to about $1.3 \times 10^8$ cfu per seed or cutting. Like the nature of the composition, a method of application such as spraying, atomizing, dusting, scattering or pouring, is chosen in accordance with the intended objectives and the prevailing circumstances.

Particularly suitable methods for applying a composition include methods that involve seed coating, soil application or incorporation into a growth medium. The number of times that a composition is applied may vary, depending on the observed or expected intensity of infestation by a particular fungal pathogen. A composition can be applied to soil as a liquid, but can also be applied to soil in granular form. Outdoor soil applications can be in furrow, broadcast, or soil injection. In greenhouse or other indoor environments, a composition can be applied by mixing with potting soils typically used in such environments. A composition may also be applied to seeds by impregnating the seeds with a liquid formulation, or coating them with a solid formulation. In various embodiments, liquid suspensions of bacteria (in water or a growth media) may be applied to seed at a rate of 5 to 10 ml per kg of seed and allowed to dry prior to bagging and storage. In special cases, further types of application are also possible, for example, selective treatment of individual plant stems or buds.

A suitable group of plants with which to practice the invention include dicots, such as safflower, alfalfa, soybean, or sunflower. Also suitable are monocots such as corn, wheat, rye, barley, or oat. Also suitable are vegetable crops or root crops such as potato, broccoli, peas, peppers, lettuce, sweet corn, popcorn, tomato, beans (including kidney beans, lima beans, dry beans, green beans) and the like. Thus, the invention has use over a broad range of plants, including species from the genera *Agroslis, Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypiuni, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panicum, Pannesetum, Persea, Phaseolus, Pistachia, Pisum, Poa, Pyrus, Prunus, Raphanus, Ricinus, Secale, Senecio, Sinapis, Solanum, Sorghum, Theobromus, Trigonella, Triticum, Vicia, Vitis, Vigna* and *Zea*.

Plant pathogenic fungi whose disease symptoms can be controlled or suppressed include *Pythium aphanidermatum, Phytophthora capsicum, Rhizoctonia solani, Fusarium graminearum, Fusarium oxysporum*, and *Alternaria solani*. Diseases associated with these fungi include damping-off and root rots of multiple plant species. The broad spectrum activity reported here further indicates the utility of the strains against most fungal and oomycete plant diseases.

EXAMPLES

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

General Methods

Standard recombinant DNA and molecular cloning techniques used in the examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found Atlas, R M (1997) *Handbook of Microbiological Media*, ed Lawrence C. Parks (CRC Press Inc., United States of America), pp 1706; *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994; or by Thomas D. Brock in *Biotechnology: A Textbook of Industrial Microbiology*, Second Edition, Sinauer Associates, Inc., Sunderland, Mass., 1989. Example Media include:

*Leptothrix* strain medium—(LM) per liter: 5 g peptone, 0.2 g magnesium sulfate heptahydrate, 0.15 g ferric ammonium citrate, 0.05 g calcium chloride, 0.01 g ferric chloride anhydrous, 0.01 g manganese sulfate monohydrate, 15 g agar.

Yeast agar van Niel's—(YAN) per liter: 10 g yeast extract, 1 g dipotassium phosphate, 0.5 g magnesium sulfate heptahydrate, 15 g agar.

Nutrient agar buffered—(NB) per liter: 4 g peptone, 4 g sodium chloride, 2 g yeast extract, 1 g beef extract, 0.45 g monopotassium phosphate, 1.78 g disodium hydrogen phosphate heptahydrate, 15 g agar.

King's Medium B—(KB) per liter: 20 g proteose peptone, 1.5 g dipotassium phosphate, 1.5 g magnesium sulfate heptahydrate, 10 ml glycerol, 15 g agar.

Cloning of MspI Generated 16s rDNA TRF

The procedure for cloning and sequencing of TRF was modified from Widmer et al (47). The 16S rDNA was amplified and digested with MspI (Promega) from multiple soil and rhizosphere DNA samples of tomato and soybean (from 14). A double stranded asymmetric adapter was ligated into the MspI site of the TRF. 5 µM MspI-adapters 1 (SEQ ID NO: 1) and 2 (SEQ ID NO: 2) (Table 1) into 1× Buffer C (Promega) and incubating 10 min at 65° C., 10 min at 37° C., 10 min at 25° C. and 10 min at 4° C. For ligation, 2 µl of the digested amplicon were mixed with 1 µl double-stranded adapter, 4.5 U T4 ligase (Promega) and 1× ligase buffer (Promega) in a 10 µl reaction. The reaction was incubated 12 h at 16° C. Following ligation, TRF were size selected from a portion of the agarose gel corresponding to 90 to 160 bp in length and purified using UltraClean GelSpin DNA Purification Kit (MoBio). The purified DNA was used to enrich the samples with 16S rDNA TRF of the target sizes. PCR was performed using 16S primer 8F (SEQ ID NO: 7) in combination with MspI-adapter primer (SEQ ID NO: 3). Amplification was carried out in 25 µl reactions containing 1× Mg-free buffer, 1.8 mM $MgCl_2$, 0.2 mM dNTPs, 1 pmol $\mu l^{-1}$ each primer, 0.04 mg $ml^{-1}$ RNase A (Novagen), 0.06 U $\mu l^{-1}$ Go Taq Flexi DNA polymerase (Promega), and 2.5 µl template. The cycling program consisted of a 5 min at 95° C. followed by 26 cycles of 94° C. for 45 s, 54° C. for 45 s, and 70° C. for 45 s; and an 8 min final extension at 70° C. The double stranded adapter was removed by digestion with MspI and the TRF-enriched samples were ligated into pGEM-T Easy Vector (Promega) prior to introduction into *E. coli* JM109 competent cells (Promega). A total of 56 transformants were selected for sequencing, based on insert size. Sequencing of this and other samples were performed at the Molecular and Cellular Imaging Center of the OARDC (Wooster, Ohio) in an ABI Prism 3100xl genetic analyzer system using 3'-BigDye dideoxynucleotide triphosphates labeling chemistry.

Extension of Target 16s rDNA TRF

The cloned TRF sequences overlap with the first variable loop region between *E. coli* positions 69-101 bp (15, www.r-na.icmb.utexas.edu). Sequence alignments were used for designing variable loop-specific primers M139F (5'-TAACGCGGGGCAACCTGGCGA-3') (SEQ ID NO: 4) and M141F (5'-CAGCACGGGAGCAATCCTGGTGG-3') (SEQ ID NO: 5) (FIG. 1). These primers were used independently in combination with universal primer 518R (SEQ ID NO: 9) to generate extended amplicons from multiple samples, with the following variations in the cycling program: 30 cycles of 94° C. for 1 min, 65° C. for 45 s, and 70° C. for 45 s. Amplicons from two independent samples were cloned, as described above, and 16 transformants were selected for sequencing.

Culture-Based Screening for M139 abd M141 Positive Isolates

A bacterial collection was generated from the rhizosphere of hay grown in soils previously described as suppressive (13, 14). The hay mix contained Festulolium duo (36% v/v), alfalfa (14%), Starfire red clover (11%), Jumbo white clover (9%), Tekapo orchard grass (9%), Tuukka timothy (9%), Lancelot plantain (6%) and chicory (6%). The hay was grown in the greenhouse with during the spring of 2007, with temperatures for the period ranging from 23° C. and 31° C. Roots and soils were thoroughly mixed, and five grams of the mixture was sampled and diluted in 50 ml of sterile water (SW). The suspension was vortexed (1 min), sonicated (1 min), and vortexed again (15 sec), and serially diluted in SW and spread-plated in *Leptothrix* strain medium (LM), Yeast agar van Niel's (YAN), Nutrient agar buffered (NB) and R2A (Difco BD). These culture media were previously reported to support the growth of various Burkholderiales species, including members of the Commamonadaceae (R2A and NB) and Genera *Incertae Sedis* (R2A, LM, YAN). Plates were incubated for 48 h at room temperature (RT) in the dark. From each plate eight colonies were picked and transferred into a 96-well plate pre-filled with 200 µl $well^{-1}$ of corresponding liquid medium. A total of 11 mixed hay pots were sampled, resulting in a collection of 704 isolates. Liquid cultures were pooled (eight per well), prior to DNA isolation performed with the Wizard Genomic DNA purification kit (Promega). DNA-pools (1:100 dilution) were PCR-screened for the presence of M139 and M141-like sequences as described above, with a 25 cycles amplification program. The primer and amplification protocol for M141 was modified (M141F2-primer: 5'-GGAGCAATCCTGGTGGCGA-3' (SEQ ID NO: 6); amplification reaction with final 1.0 mM $MgCl_2$) to maximize recovery of isolates matching the targeted variable loop sequence. Individual amplifications were performed from individual cultures present in PCR-positive pools only. Colony-PCR was performed with the 8F and 1492R primer combination (14). 16S amplicons were purified with ExoSAP-IT (USB), and sequenced. Consensus sequences for each isolate were constructed using Sequencher 4.7 (Gene Codes Corporation).

In vitro Inhibition of Pathogen Growth

Pathogen growth inhibition was tested in multiple contexts. For *Mitsuaria* isolates, assays were performed on R2A, LM and 1/10 TS agar (TSA). For *Burkholderia* isolates, R2A, LM and 1/3 King's Medium B (KB, (54)) were used. Bacteria from 48 h-old culture plates were resuspended in SW, and a 10 µl drop was placed on a plate with a test pathogen in the center. Plates were incubated at RT and growth inhibition was scored between 4-10 days, depending on the pathogen. In vitro inhibition was scored as positive or negative, though phenotypes scored as positive varied somewhat depending on the pathogen and media combination used. Positive scores reflected the formation of clear inhibition zones between the pathogen and the bacteria, diminished total growth of pathogen as compared to the control, melanization or morphology change in pathogen colony, and/or bacterial swarming over the pathogen culture. In vitro inhibition tests were performed against *Pythium aphanidermatum* isolate 349, and *Phytopthora capscici* provided by S. Miller (OARDC); *Pythium sylvaticum* 134, *Phythophthora sojae* race 25 and *Rhizoctonia solani* AG4 provided by A. Dorrance (OARDC); *F. graminearum* provided by P. Paul (OARDC); and *Alternaria solani* Mg23 and *Fusarium oxysporum* Ft25 (59).

Seedling Disease Bioassays

Soybean and tomato seeds were surface sterilized and germinated on water agar (WA; 7.5 g agar $l^{-1}$) at RT in the dark. After four days three seedlings were transferred to Petri-plates containing WA (tomato: 100×15 mm; soybean 150×15 mm). A 5 mm pathogen plug was placed in the center of the plate and seedlings were treated with ~$10^7$ cell $ml^{-1}$ $seedling^{-1}$, in ≦100 ul volume. Inoculum was prepared from 24 h cultures in 1/10×TS broth, collected by centrifugation, and washed twice with SW. Control plates with water-treated seedlings with and without pathogen inoculum were also prepared. Each plate was prepared in triplicate. Seedling disease was scored after 4 and 5 days for soybean and tomato respectively. For each (n≧9) seedling, total seedling length and lesion length were measured, and disease severity was expressed as the percent of the seedling that showed a lesion. Three bacterial isolates of each recovered genus were selected for analysis based on their independent isolation from different hay-containing pots. For *Mitsuaria* isolates, soybean assays were run against *P. aphanidermatum*, *P. sojae* and *R. solani* and for tomato against *P. aphanidermatum* and

*R. solani.* For *Burkholderia* isolates soybean and tomato assays were run against *R. solani* only. All experiments were run at least twice.

Sequence Analyses

Sequences were aligned and pair-wise comparisons calculated with ClustalW2 (EMBL-EBI Tools). Graphic alignments were prepared using Jalview (v 2.3) alignment editor. Individual sequences were compared to the non-redundant nucleotide collection NCBI database (nr/nt, as of Mar. 8, 2008) using blastn. Phylogenetic analyses were performed using MEGA 4. Tree topologies generated by different algorithms were compared and found to be equivalent (data not shown). Sequences were deposited in GenBank with Accession No. EU714905-EU714956.

Statistical Analyses

All analyses were performed using JMP v7.0 (SAS Institute Inc.). The Kruskall-Wallis test was used to determine differences in disease severity. Five treatment levels were considered: three bacterial isolates in the presence of pathogen and water treated seedlings with or without pathogen. Pair-wise comparisons were performed between individual bacteria and water treated seedlings (plus pathogen) with Wilcoxon-2-sample test. Contrast analysis (Wilcoxon-2-sample test, one tail) was performed to determine overall effect of bacterial treatment compared to water treated seedlings (plus pathogen).

EXAMPLE 1

Classification of 16S Eubacterial Sequences Corresponding in Size to a Target TRF The identity of bacteria giving rise to MspI generated TRF associated with disease suppression in the microbial community profiles (see Benítez M, et al (2007) Multiple statistical approaches of community fingerprint data reveal bacterial populations associated with general disease suppression arising from the application of different organic field management strategies. Soil Biology and Biochemistry 39, 2289-2301, incorporated by reference in its entirety) was first assessed by cloning TRF of the selected size range. Of 56 clones sequenced, 20 were confirmed as a targeted TRF (seven to M139, eight to M141 and five to M148). These sequences were compared to GenBank using blastn. Five M139 clones shared >90% sequence identity with one another, and likely arise from β-Proteobacteria; and, of these, four, recovered from three independent samples, shared >97% sequence identity to database members of the order Burkholderiales not assigned to a named family (i.e. Genera *Incertae Sedis*). Similarly, four M141 clones derived from independent samples showed a high degree of similarity to one another and were classified as Burkholderiales, but of more diverse origin. Other M141 clones differed substantially from this group (68-82% sequence identity) and among themselves (66-78% sequence identity) and might belong to the divisions Gemmatimonadetes, Acidobacteria and/or Spirochaete. The greatest sequence variation was observed within the sampled population of M148 clones, which shared only 46-71% sequence identity with each other. Two matched Proteobacteria, one matched Spirochaetae and one matched Planctomycete sequences. Within each cloned TRF subset, at least one did not show any significant similarity to any taxonomic group within GenBank. These data further support our initial hypothesis that multiple novel bacterial populations are associated with the suppressive activity developing from the hay-based transition strategy.

The cloned M139 and M141 TRF were used to recover longer and more phylogenetically informative sequences from the suppressive soils. Among these, over half of the TRF likely arose from novel bacterial species not previously associated with plant disease suppression (i.e. Burkholderiales, Genera *Incertae Sedis*). Sequence alignments of known Burkholderiales species and M139 and M141 clones revealed sequence variation within the first variable loop of the 16S rRNA (15), and this data was used to design M139- and M141-specific primers (FIG. 1; Table 1). These primers were used in combination with eubacterial primer 518R (SEQ ID NO: 9) to generate extended amplicons from two DNA samples from 14. Four of the M139-extended sequences showed similarity to bacteria of the Genera *Incertae Sedis* (four genera with >97% identity) and three M141 matched Comamonadaceae (2 genera with >97% identity).

Sequences from both cloning steps were aligned to assemble consensus sequences. For M139, three different consensus sequences with 100% identity over a 76 nt overlap were constructed. Based on approximately 520 nt, the three M139 constructed sequences exhibited >97% identity to database entries of Genera *Incertae Sedis Leptothrix, Ideonella* and *Methylibium*, respectively. In addition, one M141 consensus sequence was constructed (97% sequence identity on a 78 nt overlap) which exhibited <97% sequence identity to database entries of the Comamonadaceae. Sequence analysis revealed the presence of a MspI recognition site that will produce a TRF of 139 bp in the three Genera *Incertae Sedis*-like assembled sequences. The Comamonadaceae-like sequence, however, lacked the MspI site to produce the expected 141 bp TRF. It is unclear if this lack of consistency reflects a high degree of sequence diversity amongst the bacteria giving rise to the targeted TRF in our samples or amplification artifacts.

EXAMPLE 2

Culture-Collection Screening for M139 and M141 Isolates

Figure 2:
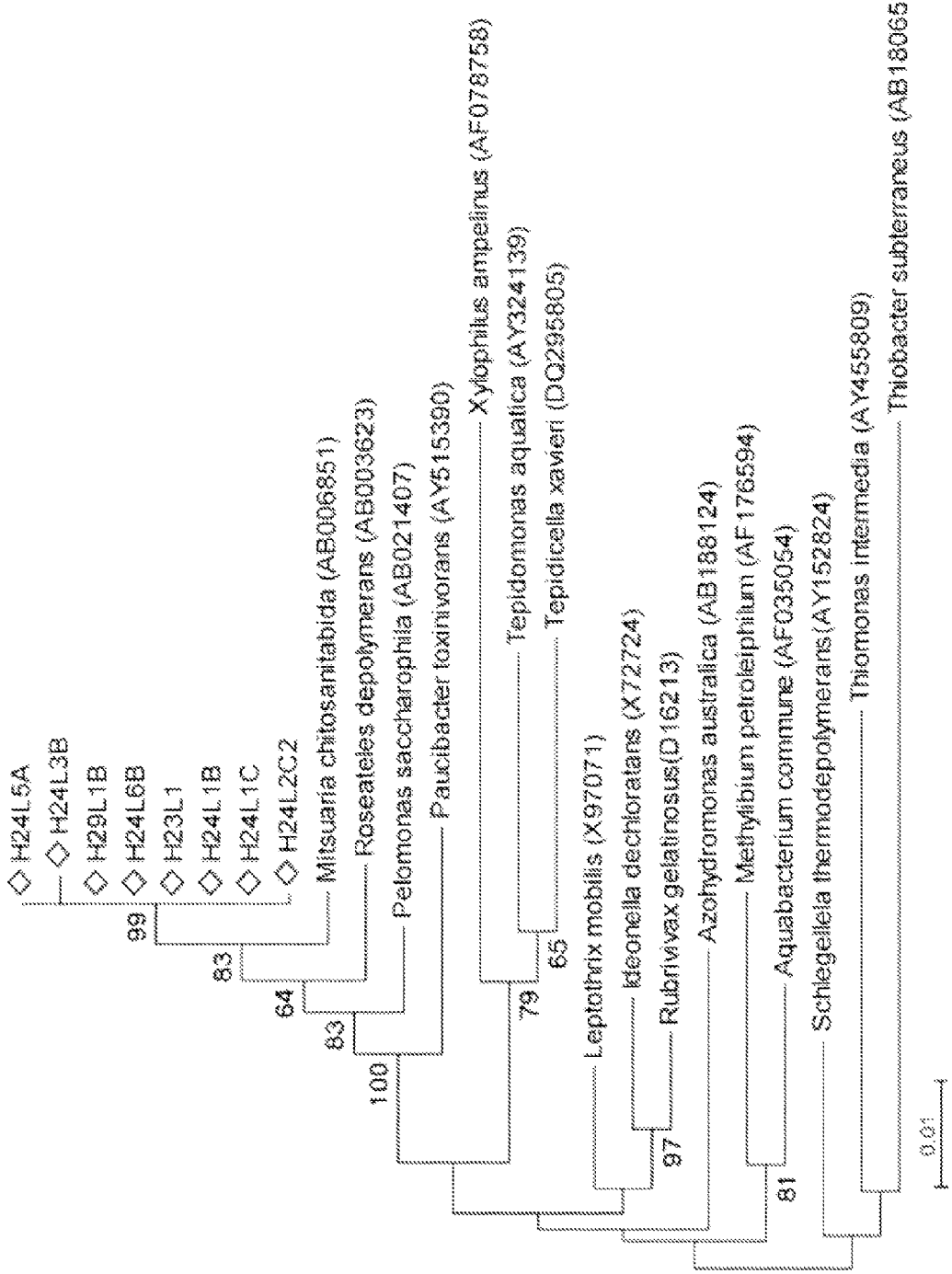
FIG. 2 is a classification chart of the M139-associated isolates (□) as *Mitsuaria* sp. based on 16S rDNA sequence analyses. Included in the dendrogram are the sequence of the type strains representative of other species of Genera *incertae* of the order Burkholderiales. The phylogenetic relationships among taxa were inferred from ~1200 bp of the 16S rDNA gene, using the Neighbor-Joining method from distances computed by the Maximum Composite Likelihood algorithm. Bootstrap values >60% (1000 replicates) are shown next to the branches. Accession numbers for each sequence are shown in parenthesis. Scale bar: number of base substitutions per site.

Because no isolates with 100% sequence identity to the cloned markers had been previously identified, efforts were made to recover bacteria giving rise to the M139 and M141 markers. To do so, culture media favoring growth of Burkholderiales species related to the genera described above were selected. The isolates were obtained from the mixture of hay species that had resulted in damping-off suppression, and a 2-step PCR-based approach was used to screen the collection, first from pooled samples and then individually. Of the 704 isolates examined, eight, all isolated from *Leptothrix* strain medium had an exact sequence match to the M139 variable loop. The highest BLAST hit to a named species for all eight isolates was to *Mitsuaria chitosanitabida* (98-99% identity), followed by *Roseateles depolymerans* and *Pelomonas aquatica* or *P. saccarophila* (>97% identity), all belonging to the Genera *Incertae Sedis*. Sequence identity within the isolates ranged from 98-100%, and their phylogenetic relationships to representative type strains of Genera *Incertae Sedis* (Burkholderiales) are shown in FIG. 2. The type strain most closely related to the isolates retrieved from the mixed species hay soils is *M. chitosanitabida* 3001 (17), but there is a clear distinction between known *Mitsuaria* species and the isolates from this study.

While the novel *Mitsuaria* isolates recovered from the disease-suppressive soil were found to have 16S sequences that similar to the initial M139 clones, they were not identical. The isolates shared just 99% identity to a *Mitsuaria*-like extended sequence clones. *Mitsuaria* species, also, do not produce an M139 in vitro or in silico. In contrast, the MspI TRF for the isolates was 487 nt (488 nt expected from sequence). Interestingly, M488 and M489 TRF were common in the TRF profiles of the studied soils, and positive associations between M488 and M489 and soilborne disease suppression were observed in two of the studied contexts (14). Variation in TRF size could relate to amplification artifacts resulting from sampling complex mixtures of closely related bacteria, as well as to the presence of pseudo-terminal restriction fragments in the samples (18). Given the sequence similarity between *Mitsuaria* isolates and M139 clones it seems likely that these represent bacteria very closely related to those giving rise to the M139 TRF associated with disease suppression.

Figure 3:
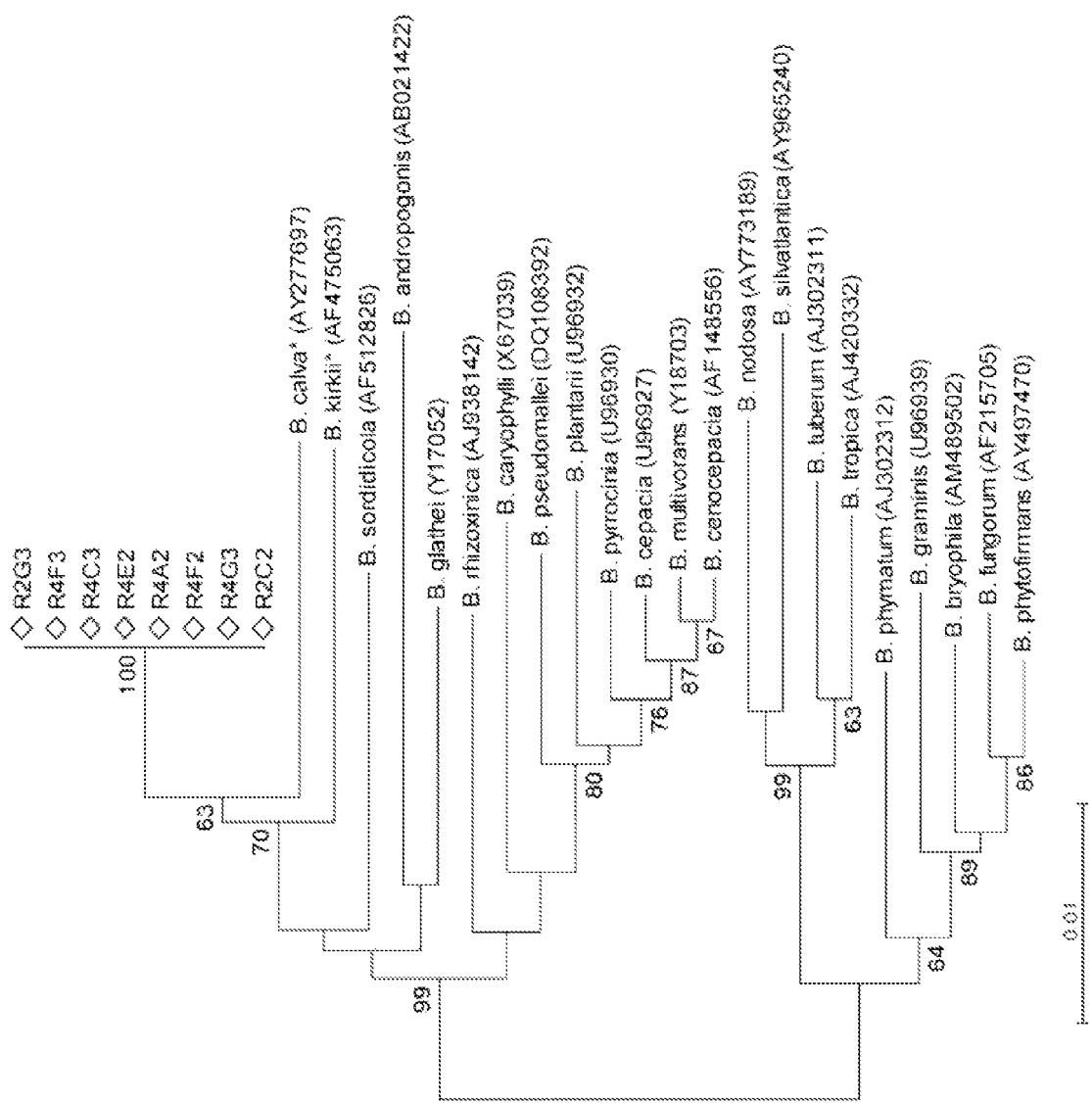
FIG. 3 is a classification chart of M141-associated isolates (◊) as a novel *Burkholderia* sp. based on 16S rDNA sequence analyses. Included in the dendrogram are the sequence of the other 22 named *Burkholderia* species. The phylogenetic relationship among taxa was inferred from ~1300 bp of the 16S rDNA gene, using the Neighbor-Joining method from distances computed by the Maximum Composite Likelihood algorithm. Bootstrap values >60% (1000 replicates) are shown next to the branches. Accession numbers for each sequence are shown in parenthesis. Scale bar: number of base substitutions per site. *Candidatus Burkholderia* species with no cultured isolate.

A similar isolation strategy led to the recovery of eight pure cultures from R2A media with an M141-like amplification profile. The 16S sequences amplified from these isolates shared 24 of the 26 nt of the M141-derived variable loop sequence. The highest BLAST hit for all eight was to unclassified *Burkholderia* spp. (i.e. 99% identity to GenBank AY238505, AB025790, and AB298718). Sequence identity within the eight isolates was >99%, but was only 96% identical to the type strain of the genus, *B. cepacia* (GenBank U96927). The isolates from this study form a phylogenetically-distinct cluster within the genus (FIG. 3), with their closest relatives being *Candidatus Burkholderia* spp., non-cultured endosymbionts from leaf galls (19, 20; 97% identical). Sequence analysis revealed 97% identity between our *Burkholderia* isolates and the initial M141 clones, but only 72-88% sequence identity with clones of the ~450 nt extended sequences. Still, the observed 16S rDNA MspI TRF for the isolates was a 139/141 bp double-peak, indicating that at least one group of bacteria with an M141 TRF was successfully isolated.

EXAMPLE 3

Characterization of Pathogen Inhibition and Disease Suppressive Activities

The association of the M139 and M141 TRF with in situ soilborne disease suppression (14) led us to hypothesize that the novel *Mitsuaria* and *Burkholderia* isolates obtained would express antagonistic activities towards diverse soilborne pathogens. Initially, the capacity of the isolates to reduce pathogen growth in vitro against was assayed. For the *Mitsuaria* isolates, inhibition was observed regardless of the pathogen tested (FIG. 4A), with the greatest frequency of inhibition expressed against *Pythium aphanidermatum Phytophthora sojae*, *Rhizoctonia solani*, and *Alternaria solani*, and the least against *Pythium sylvaticum*.

Figure 5:
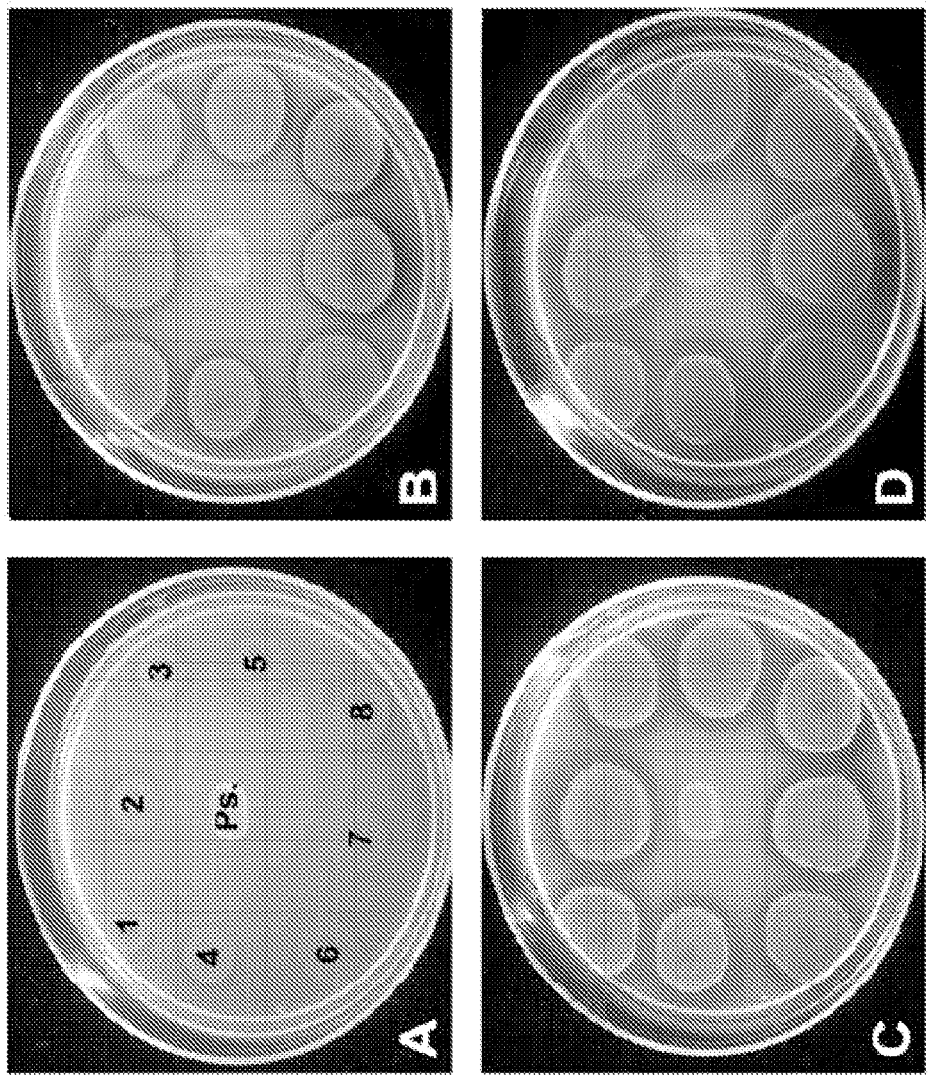
FIG. 5 shows experimental photographs demonstrating the chitinolytic activity of *Mitsuaria* isolates.

All of the *Mitsuaria* isolates from this study have chitinolytic activity in vitro (FIG. 5), which can relate to the broad-spectrum inhibition observed against the various fungi. Briefly, for each isolate tested (1-8) 7 μl of bacterial suspension (in water) were spotted on 1/10 TS agar plates amended with 0.2% colloidal chitin. Plates were incubated at room temperature in the dark and observations were recorded at A) 2, B) 5, C) 7 and D) 9 days after inoculation. *Pseudomonas fluorescens* (Ps., straind wood1R) was used as a negative control for chitinolytic activity. 1: H24LB; 2: H23L1; 3: H24L1C; 4: H24L2C2; 5: H29L1B; 6: H24L5A; 7: H24L6B; 8: H24L3B. Protocol for preparation of colloidal chitin was modified from Rodriguez-Kabana et al. (1983; Plant Soil 75, 95-106) and Shimahara and Takiguchi (1988; Meth Enzymol 161, 417). Briefly, 20 ml of 10N HCl were added to 0.5 g of chitin (Sigma C8908) and stirred constantly for 2 h. The colloidal chitin was thoroughly washed with water, with three over night steps. When suspension reached to pH 6.0 colloidal chitin was resuspended in 200 ml water and stored at 10° C. until use.

Figure 4:
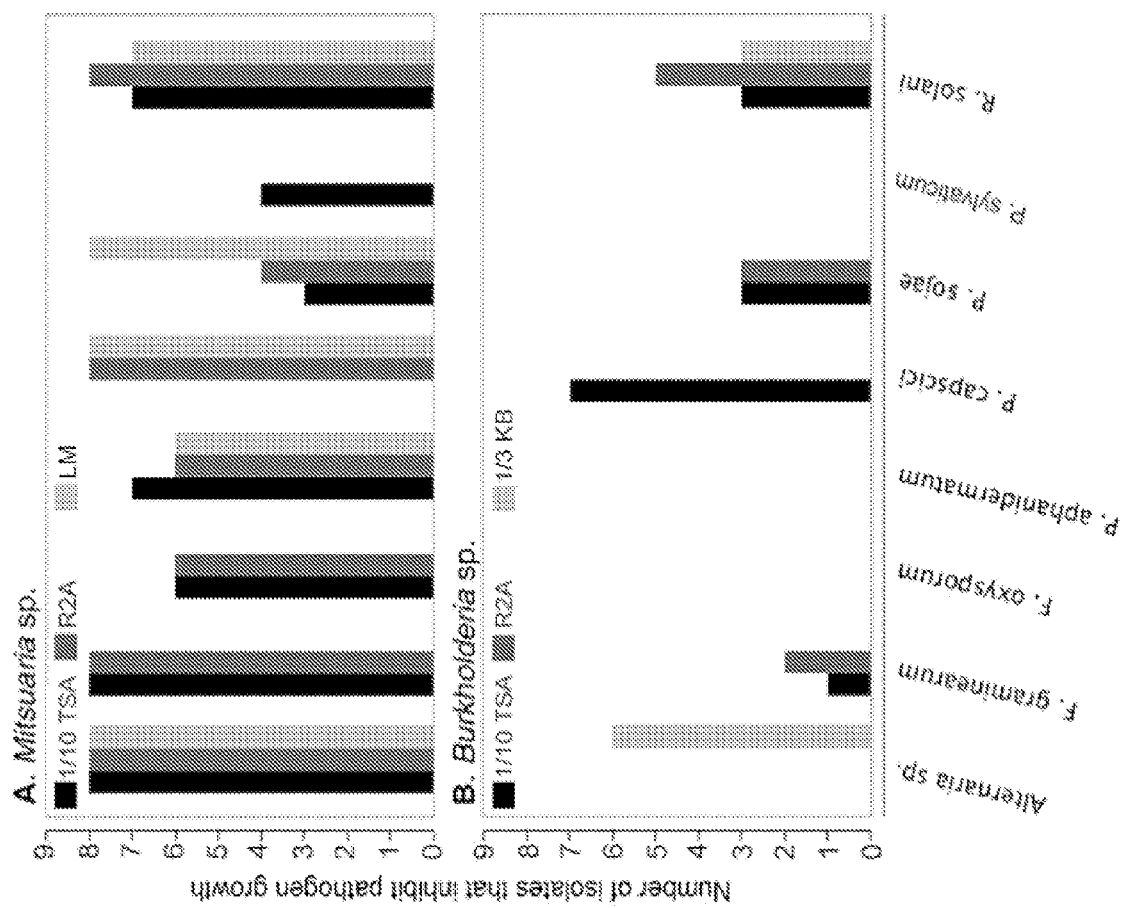
FIG. 4 is a graph of the frequency of positive in-vitro inhibition activity of *Mitsuaria* (A) and *Burkholderia* (B) isolates identified in this study against multiple fungal and oomycete tomato and soybean pathogens. In-vitro inhibition activity was tested for eight isolates of each genus on three different media and was scored as positive or negative. TSA, trypticase soy agar; R2A, R2A media for growth of heterotrophic organisms; KB, King's medium B; LM, *Leptothrix* strain medium.

Even so, other mechanisms must be involved in the inhibition of the oomycetes which do not harbor chitin as a major component in their cell walls (21). Similar assays were performed with other *Mitsuaria* spp. including multiple chitosan-degrading strains isolated from soils in Japan (ATCC type strain *M. chitosanitabida* 3001, strain 12 and strain 13, 17) and gallic acid degrading strains associated to freshwater plants (*Mitsuaria* spp.: FBTS 25 and FBTS 19, 22). Of these, chitosan-degrading strains 12 and 13 showed a similar spectrum of inhibition; whereas the type strain 3001 gave a positive inhibition in only about half of the assays. While the sequence identity with the tested Japanese strains was ≧98%, the antagonistic phenotype of our isolates was less variable. The *Mitsuaria* strains recovered from freshwater plants expressed no pathogen inhibition in most cases. Among the *Burkholderia* isolates, in vitro pathogen inhibition was less frequent and more variable (FIG. 4B). Significant variation in the expressed inhibitory capacities was observed among isolates, with six isolates inhibiting at least three pathogens, but none of these inhibited the same three pathogens. In contrast to *Mitsuaria* isolates, all eight *Burkholderia* isolates tested negative for chitinolytic activity.

Seedling diseases were suppressed by inoculation with the novel *Mitsuaria* isolates. All the tested isolates reduced disease severity in soybeans challenged with *P. aphanidermatum* (P=0.03 and 0.005) and in tomato challenged with *P. aphanidermatum* (P=0.0003 and 0.002) and *R. solani* (P=0.27, 0.02 and 0.0007). Although not significant for most experiments, the lesion severity caused by *R. solani* was also reduced by the *Mitsuaria* isolates in three separate assays. Overall, disease severity reductions ranged from 5 to 20 percent (see e.g., Table 2).

TABLE 2

Lesion severity in soybean and tomato seedlings treated with *Mitsuaria* isolates and challenged with damping-off pathogens

| Crop | Treatment | Lesion severity[a] | |
|---|---|---|---|
| | | *P. aphanidermatum* | *R. solani* |
| Soybean | H23L1 | 44.2[b]**[d] | 22.9 |
| | H24L5A | 62.5* | 26.7 |
| | H29L1B | 64.3 | 33.3 |
| | Pathogen only | 91 | 32.2 |
| | No Pathogen | 27 | 11.7 |
| | K-W test[c] | P < 0.0001 | P = 0.0002 |
| Tomato | H23L1 | 57.8** | 45** |
| | H24L5A | 41.7*** | 33.3*** |
| | H29L1B | 60.4** | 33.3*** |
| | Pathogen only | 91.7 | 55.6 |
| | No Pathogen | 47.7 | 34.8 |
| | K-W test | P = 0.019 | P = 0.006 |

[a]Lesion severity, percent of lesion length in relation to seedling length
[b]Median values are reported, for n = 16 (soybean/*R. solani*) or n = 12 (others)
[c]Non-parametric Kruskall-Wallis test was used to assess differences among all five treatments
[d]Significant pairwise comparisons between treatment and pathogen only control at *P < 0.01, P < 0.05 and *P < 0.1 (Wilcoxon 2-sample test).

Though the data represented in Table 2 represent one assay, comparable patterns were observed across experiments. In 7 out of the 11 tests, treatment with *Mitsuaria* isolate H24L5A resulted in lower disease severity than the water treated control, whereas isolates H23L1 and H29L1B resulted in disease severity reduction in 4 out of the 11 tests, with greatest variation observed in the soybean bioassays (data not shown).

Similarly, seedling disease severity, caused by *R. solani* was reduced on tomato and soybeans inoculated with *Burkholderia* isolates. As a group, disease severity was reduced by at least 15% on soybean (P=0.0001 and 0.0005) and 20% on tomato seedlings (P<0.0001 for both tests) compared to the water treated control (Table 3).

TABLE 3

Lesion severity in soybean and tomato seedlings treated with *Burkholderia* strains and challenged with *Rhizoctonia solani*

| Crop | Treatment | Lesion severity[a] |
|---|---|---|
| Soybean | R2C2 | 36.1[b***d] |
|  | R2G3 | 34.5*** |
|  | R4F2 | 34.2** |
|  | Pathogen only | 56.1 |
|  | No pathogen | 29.1 |
|  | K-W test[c] | P = 0.003 |
| Tomato | R2C2 | 46.2*** |
|  | R2G3 | 42.3*** |
|  | R4F2 | 48.3*** |
|  | Pathogen only | 63.6 |
|  | No pathogen | 45.2 |
|  | K-W test | P = 0.002 |

[a]Lesion severity, percent of lesion length in relation to seedling length
[b]Median values are reported for n = 12
[c]Non-parametric Kruskall-Wallis test was used to assess differences among all five treatments
[d]Significant pairwise comparisons between treatment and pathogen only control at *P < 0.01 and P < 0.05 (Wilcoxon 2-sample test).

For the *Burkholderia* isolates tested, no apparent variation in their ability to reduce lesion severity was observed. Overall these data support the hypothesis that multiple isolates of novel *Mitsuaria* and *Burkholderia* species contribute to the general soilborne disease suppression induced by the mixed hay cropping system.

The following documents are hereby incorporated by reference (there is no admission thereby made with respect to whether any of the documents constitute prior art with respect to any of the claims):

1. Torsvik V & Ovreas L (2002) Microbial diversity and function in soil: From genes to ecosystems. *Curr Opin Microbiol* 5, 240-245.
2. Daniel R (2005) The metagenomics of soil. *Nature Reviews Microbiology* 3, 470-478.
3. Van Lanen S G & Shen B (2006) Microbial genomics for the improvement of natural product discovery. *Curr Opin Microbiol* 9, 252-260.
4. Maron P A, Ranjard L, Mougel C & Lemanceau P (2007) Metaproteomics: A new approach for studying functional microbial ecology. *Microb Ecol* 53, 486-493.
5. Martin H G, et al (2006) Metagenomic analysis of two enhanced biological phosphorus removal (EBPR) sludge communities. *Nat Biotechnol* 24, 1263-1269.
6. Miller S R, et al (2005) Discovery of a free-living chlorophyll d-producing cyanobacterium with a hybrid proteobacterial/cyanobacterial small-subunit rRNA gene. *Proceedings of the National Academy of Sciences* 102, 850-855.
7. Adesina M F, Lembke A, Costa R, Speksnijder A & Smalla K (2007) Screening of bacterial isolates from various european soils for in vitro antagonistic activity towards *Rhizoctonia solani* and *Fusarium oxysporum*: Site-dependent composition and diversity revealed. *Soil Biology and Biochemistry* 39, 2818-2828.
8. Mazzola M (2004) Assessment and management of soil microbial community structure for disease suppression. *Annu Rev Phytopathol* 42, 35-59.
9. Borneman J & Becker J O (2007) Identifying microorganisms involved in specific pathogen suppression in soil. *Annu Rev Phytopathol* 45, 153-172.
10. Baker K F (1987) Evolving concepts of biological control of plant pathogens. *Annu Rev Phytopathol* 25, 67-85.
11. Weller D M, Raaijmakers J M, McSpadden Gardener B B & Thomashow L S (2002) Microbial populations responsible for specific soil suppressiveness to plant pathogens. *Annu Rev Phytopathol* 40, 309-348.
12. Garbeva P, Postma J, van Veen J A & van Elsas J D (2006) Effect of above-ground plant species on soil microbial community structure and its impact on suppression of *Rhizoctonia solani* AG3. *Environ Microbiol* 8, 233-246.
13. Baysal F, Benitez M, Kleinhenz M D, Miller S A & McSpadden Gardener B B (2008) Field management effects on damping-off and early season vigor of crops in a transitional organic cropping system. *Phytopathology* 98, 562-570.
14. Benítez M, et al (2007) Multiple statistical approaches of community fingerprint data reveal bacterial populations associated with general disease suppression arising from the application of different organic field management strategies. *Soil Biology and Biochemistry* 39, 2289-2301.
15. Cannone J J, et al (2002) The comparative RNA web (CRW) site: An online database of comparative sequence and structure information for ribosomal, intron, and other RNAs. *BMC Bioinformatics* 3, 2.
16. Muyzer G, de Waal E C & Uitterlinden A G (1993) Profiling of complex microbial populations by denaturing gradient gel electrophoresis analysis of polymerase chain reaction-amplified genes coding for 16S rRNA. *Appl Environ Microbiol* 59, 695-700.
17. Amakata D, et al (2005) *Mitsuaria chitosanitabida* gen. nov., sp nov., an aerobic, chitosanase-producing member of the 'Betaproteobacteria'. *Int J Syst Evol Microbiol* 55, 1927-1932.
18. Liu, W & Stahl, D A (2007) in *Manual of Environmental Microbiology*, eds. Hurst C J, et al (ASM Press) pp 139-156.
19. Van Oevelen S, De Wachter R, Vandamme P, Robbrecht E & Prinsen E (2002) Identification of the bacterial endosymbionts in leaf galls of *Psychotria* (Rubiaceae, Angiosperms) and proposal of '*Candidatus Burkholderia kirkii*' sp nov. *Int J Syst Evol Microbiol* 52, 2023-2027.
20. Van Oevelen S, De Wachter R, Vandamme P, Robbrecht E & Prinsen E (2004) '*Candidatus Burkholderia calva*' and '*Candidatus Burkholderia nigropunctata*' as leaf gall endosymbionts of african *psychotria*. *Int J Syst Evol Microbiol* 54, 2237-2239.
21. Bartnicki-Garcia S (1968) Cell wall chemistry, morphogenesis, and taxonomy of fungi. *Annu Rev Microbiol* 22, 87.
22. Muller N, Hempel M, Philipp B & Gross E M (2007) Degradation of gallic acid and hydrolysable polyphenols is constitutively activated in the freshwater plant-associated bacterium *Matsuebacter* sp FB25. *Aquat Microb Ecol* 47, 83-90.
23. Yun C S, Amakata D, Matsuo Y, Matsuda H & Kawamukai M (2005) New chitosan-degrading strains that produce chitosanases similar to ChoA of *Mitsuaria chitosanitabida*. *Appl Environ Microbiol* 71, 5138-5144.
24. Kaiser O, Puhler A & Selbitschka W (2001) Phylogenetic analysis of microbial diversity in the rhizoplane of oilseed 25. Gomila M, et al (2005) Identification of culturable bacteria present in haemodialysis water and fluid. *FEMS Microbiol Ecol* 52, 101-114.
26. Malmqvist A, et al (1994) Ideonella dechloratans gen. nov., sp. nov., a new bacterium capable of growing anaerobically with chlorate as an electron acceptor. *Syst Appl Microbiol* 17, 58.
27. Siering P L & Ghiorse W C (1996) Phylogeny of the Sphaerotilus-Leptothrix group inferred from morphological comparisons, genomic fingerprinting, and 16S ribosomal DNA sequence analyses. *Int J Syst Bacteriol* 46, 173-182.
28. Xie C H & Yokota A (2005) Reclassification of *Alcaligenes latus* strains IAM 12599 (T) and IAM 12664 and *Pseudomonas saccharophila* as *Azohydromonas lata* gen. nov., comb. nov., *Azohydromonas australica* sp nov and *Pelomonas saccharophila* gen. nov., comb. nov., respectively. *Int J Syst Evol Microbiol* 55, 2419-2425.
29. Gomila M, Bowien B, Falsen E, Moore E R B & Lalucat J (2008) Description of *Roseateles aquatilis* sp. nov. and *Roseateles terrae* sp. nov., in the class Betaproteobacteria, and emended description of the genus *Roseateles*. *Int J Syst Evol Microbiol* 58, 6-11.
30. Kadivar H & Stapleton A (2003) Ultraviolet radiation alters maize phyllosphere bacterial diversity. *Microb Ecol* 45, 353.
31. Roesch L, Camargo F, Bento F & Triplett E (2008) Biodiversity of diazotrophic bacteria within the soil, root and stem of field-grown maize. *Plant Soil* 302, 91-104.
32. Coelho R, et al (2008) Diversity of nifH gene pools in the rhizosphere of two cultivars of sorghum (*Sorghum bicolor*) treated with contrasting levels of nitrogen fertilizer. *FEMS Microbiol Lett* 279, 15.
33. Macur R E, Wheeler J T, Burr M D & Inskeep W P (2007) Impacts of 2,4-D application on soil microbial community structure and on populations associated with 2,4-D degradation. *Microbiological Research*, 162, 37-45.
34. Hayatsu M, Hirano M & Tokuda S (2000) Involvement of two plasmids in fenitrothion degradation by *Burkholderia* sp. strain NF100. *Appl Environ Microbiol* 66, 1737-1740.
35. Kikuchi Y, Hosokawa T & Fukatsu T (2007) Insect-microbe mutualism without vertical transmission: A stinkbug acquires a beneficial gut symbiont from the environment every generation. *Appl Environ Microbiol* 73, 4308-4316.
36. Murray R & Stackebrandt E (1995) Taxonomic note: Implementation of the provisional status *Candidatus* for incompletely described procaryotes. *Int J Syst Bacteriol* 45, 186-187.
37. Coenye T & Vandamme P (2003) Diversity and significance of *Burkholderia* species occupying diverse ecological niches. *Environ Microbiol* 5, 719-729.
38. Parke J L & Gurian-Sherman D (2001) Diversity of the *Burkholderia cepacia* complex and implications for risk assessment of biological control strains. *Annu Rev Phytopathol* 39, 225-258.
39. el-Banna N & Winkelmann G (1998) Pyrrolnitrin from *Burkholderia cepacia*: Antibiotic activity against fungi and novel activities against streptomycetes. *J Appl Microbiol* 85, 69.
40. Caballero-Mellado J, Onofre-Lemus J, Estrada-de los Santos P & Martinez-Aguilar L (2007) The tomato rhizosphere, an environment rich in nitrogen-fixing *Burkholderia* species with capabilities of interest for agriculture and bioremediation. *Appl Environ Microbiol* 73, 5308-5319.
41. Perin L, et al (2006) Diazotrophic *Burkholderia* species associated with field-grown maize and sugarcane. *Appl Environ Microbiol* 72, 3103-3110.
42. Salles J F, Samyn E, Vandamme P, van Veen J A & van Elsas J D (2006) Changes in agricultural management drive the diversity of *Burkholderia* species isolated from soil on PLAT medium. *Soil Biology & Biochemistry* 38, 661-673.
43. Salles J F, van Elsas J D & van Veen J A (2006) Effect of agricultural management regime on *Burkholderia* community structure in soil. *Microb Ecol* 52, 267-279.
44. Bankhead S B, Landa B B, Lutton E, Weller D M & McSpadden Gardener B B (2004) Minimal changes in rhizobacterial population structure following root colonization by wild type and transgenic biocontrol strains. *FEMS Microbiol Ecol* 49, 307-318.
45. McSpadden Gardener B B & Weller D M (2001) Changes in populations of rhizosphere bacteria associated with take-all disease of wheat. *Appl Environ Microbiol* 67, 4414-4425.
46. Nakanishi Y, et al (2006) Increase in terminal restriction fragments of bacteroidetes-derived 16S rRNA genes after administration of short-chain fructooligosaccharides. *Appl Environ Microbiol* 72, 6271-6276.
47. Widmer F, Hartmann M, Frey B & Kolliker R (2006) A novel strategy to extract specific phylogenetic sequence information from community T-RFLP. *J Microbiol Methods* 66, 512-520.
48. Cadillo-Quiroz H, Yashiro E, Yavitt J B & Zinder S H (2008) Characterization of the archaeal community in a minerotrophic fen and Terminal restriction fragment length polymorphism-directed isolation of a novel hydrogenotrophic methanogen. *Appl Environ Microbiol* 74, 2059-2068.
49. Jeon C O, et al (2003) Discovery of a bacterium, with distinctive dioxygenase, that is responsible for in situ biodegradation in contaminated sediment. *Proceedings of the National Academy of Sciences* 100, 13591-13596.
50. Yin B, Valinsky L, Gao X B, Becker J O & Borneman J (2003) Identification of fungal rDNA associated with soil suppressiveness against *Heterodera schachtii* using oligonucleotide fingerprinting. *Phytopathology* 93, 1006-1013.
51. Olatinwo R, Yin B, Becker J O & Borneman J (2006) Suppression of the plant-parasitic nematode *Heterodera schachtii* by the fungus *Dactylella oviparasitica*. *Phytopathology* 96, 111-114.
52. Valinsky, et al (2002) Analysis of bacterial community composition by oligonucleotide fingerprinting of rRNA genes. *Appl Environ Microbiol* 68, 3243.
53. Leveau J H J (2007) The magic and menace of metagenomics: Prospects for the study of plant growth-promoting rhizobacteria. *Eur J Plant Pathol* 119, 279-300.
54. Atlas, R M (1997) *Handbook of Microbiological Media*, ed Lawrence C. Parks (CRC Press Inc., United States of America), pp 1706.
55. Kampfer P, et al (1996) Characterization of bacterial communities from activated sludge: Culture-dependent numerical identification versus in situ identification using group- and genus-specific rRNA-targeted oligonucleotide probes. *Microb Ecol* 32, 101-121.
56. Massa S, Caruso M, Trovatelli F & Tosques M (1998) Comparison of plate count agar and R2A medium for enumeration of heterotrophic bacteria in natural mineral water. *World J Microbiol Biotechnol* 14, 727-730.

57. Kampfer P (1997) Detection and cultivation of filamentous bacteria from activated sludge. *FEMS Microbiol Ecol* 23, 169-181.
58. *Bergey's manual of systematic bacteriology* (2005), eds Boone D R, Castenholz R W & Garrity G M (Springer, New York).
59. Chapin L, Wang Y, Lutton E, McSpadden Gardener B B (2006) Distribution and fungicide sensitivity of fungal pathogens causing anthracnose-like lesions on tomatoes grown in Ohio. *Plant Dis* 90, 397.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising about $10^3$ cfu to about $10^{11}$ cfu of a bacterial strain per gram dry inert carrier, wherein said bacterial strain is designated from the group consisting of H24L5A, deposited as ATCC Accession Number PTA-10183, and R4F2, deposited as ATCC Accession No. PTA-10182.

2. The composition of claim 1, wherein said bacterial strain is designated R4F2, deposited as ATCC Accession Number PTA-10182.

3. The composition of claim 2, further comprising about 1% to about 40% growth medium per gram of the carrier on a wt/wt dry basis.

4. The composition of claim 2, wherein said bacterial strain exhibits plant pathogen suppression.

5. The composition of claim 2, wherein said bacterial strain exhibits fungicidal or fungistatic activity when applied to plant material or the soil environment.

6. The composition of claim 2, wherein said bacterial strain exhibits fungicidal or fungistatic activity towards a fungal or oomycete plant pathogen in situ.

7. The composition of claim 1, further comprising about 1% to about 40% growth medium per gram of the carrier on a wt/wt dry basis.

8. The composition of claim 1, wherein said bacterial strain exhibits plant pathogen suppression.

9. The composition of claim 1, wherein said bacterial strain exhibits fungicidal or fungistatic activity when applied to plant material or the soil environment.

10. The composition of claim 1, wherein said bacterial strain exhibits fungicidal or fungistatic activity towards a fungal or oomycete plant pathogen in situ.

11. A method of controlling the growth of a plant pathogenic fungus, comprising applying to a plant a composition comprising a bacterial strain, the composition exhibits fungicidal or fungistatic activity towards said plant pathogenic fungus, wherein symptoms of a disease caused by said fungus are suppressed on said plant, and wherein the bacterial strain is selected from a group consisting of the bacterial strain designated H24L5A, deposited as ATCC Accession Number PTA-10183;

the bacterial strain designated R4F2, deposited as ATCC Accession Number PTA-10182;

the bacterial strain comprises a nucleic acid, the nucleic acid comprising a sequence having at least 97% identity with SEQ ID NO: 10;

the bacterial strain comprises a nucleic acid, the nucleic acid comprising a sequence having at least 97% identity with SEQ ID NO: 19;

the bacterial strain comprises genomic DNA with a 16S sequence indicative of the bacterial species of the strain designated H24L5A, deposited as ATCC Accession Number PTA-10183, and
the bacterial strain comprises genomic DNA with a 16S sequence indicative of the bacterial species of the strain designated R4F2, deposited as ATCC Accession Number PTA-10182.

* * * * *

UNITED STATES PATENT AND TRADEMARK OFFICE
CERTIFICATE OF CORRECTION

PATENT NO. : 8,404,475 B2
APPLICATION NO. : 13/055672
DATED : March 26, 2013
INVENTOR(S) : McSpadden Gardener et al.

It is certified that error appears in the above-identified patent and that said Letters Patent is hereby corrected as shown below:

In the Specification

In column 7, line 54, delete "BLASTIN" and insert -- BLASTN --.

In column 14, line 22, delete "Sedis Leptothrix" and insert -- Sedis: Leptothrix --.

Signed and Sealed this
Twenty-second Day of October, 2013

Teresa Stanek Rea
*Deputy Director of the United States Patent and Trademark Office*